(12) United States Patent
Velo

(10) Patent No.: US 11,291,401 B2
(45) Date of Patent: Apr. 5, 2022

(54) ARRHYTHMIA MONITORING USING PHOTOPLETHYSMOGRAPHY

(71) Applicant: Salutron, Inc., Newark, CA (US)

(72) Inventor: Lino Velo, San Ramon, CA (US)

(73) Assignee: Salutron, Inc., Newark, CA (US)

( * ) Notice: Subject to any disclaimer, the term of this patent is extended or adjusted under 35 U.S.C. 154(b) by 280 days.

(21) Appl. No.: 16/146,464

(22) Filed: Sep. 28, 2018

(65) Prior Publication Data

US 2020/0100693 A1 Apr. 2, 2020

Related U.S. Application Data

(60) Provisional application No. 62/567,683, filed on Oct. 3, 2017.

(51) Int. Cl.
| | |
|---|---|
| *A61B 5/361* | (2021.01) |
| *A61B 5/00* | (2006.01) |
| *G16H 50/20* | (2018.01) |
| *A61B 5/0205* | (2006.01) |
| *G06N 20/00* | (2019.01) |

(Continued)

(52) U.S. Cl.
CPC .......... *A61B 5/361* (2021.01); *A61B 5/02055* (2013.01); *A61B 5/282* (2021.01); *A61B 5/333* (2021.01); *A61B 5/486* (2013.01); *A61B 5/681* (2013.01); *A61B 5/746* (2013.01); *G06N 20/00* (2019.01); *G16H 50/20* (2018.01); *A61B 5/01* (2013.01); *A61B 5/0255* (2013.01); *A61B 5/02108* (2013.01); *A61B 5/02405* (2013.01); *A61B 5/02416* (2013.01); *A61B 5/02438* (2013.01); *A61B 5/0533* (2013.01); *A61B 5/1118* (2013.01); *A61B 5/7267* (2013.01); *A61B 5/7278* (2013.01); *A61B 5/7282* (2013.01); *A61B 5/7285* (2013.01); *A61B 2562/066* (2013.01)

(58) Field of Classification Search
CPC ...... A61B 5/02055; A61B 5/046; A61B 5/681
See application file for complete search history.

(56) References Cited

U.S. PATENT DOCUMENTS

| | | |
|---|---|---|
| 8,509,882 B2 | 8/2013 | Albert et al. |
| 9,839,363 B2 | 12/2017 | Albert |

(Continued)

*Primary Examiner* — Joseph M Dietrich
(74) *Attorney, Agent, or Firm* — Vierra Magen Marcus LLP

(57) ABSTRACT

Described herein are user-wearable devices, and methods for use therewith, for monitoring for one or more types of arrhythmias based on a photoplethysmography (PPG) signal obtained using an optical sensor of a user-wearable device. A PPG based statistical and/or machine learning model is used to analyze a PPG signal, obtained using the optical sensor, to monitor for one or more types of arrhythmias including atrial fibrillation (AF). In response to detecting an arrhythmia based on the PPG signal, an electrocardiogram (ECG) signal is obtained using an ECG sensor of the user-wearable device. An ECG based statistical and/or machine learning model is used to analyze the ECG signal obtained using the ECG sensor of the user-wearable device to confirm or reject the arrhythmia detected based on the PPG signal and/or to perform arrhythmia discrimination. Obtained PPG and/or ECG signal segments can be provided to the model(s) to update the model(s).

31 Claims, 6 Drawing Sheets

(51) Int. Cl.
*A61B 5/282* (2021.01)
*A61B 5/333* (2021.01)
*A61B 5/01* (2006.01)
*A61B 5/024* (2006.01)
*A61B 5/0533* (2021.01)
*A61B 5/11* (2006.01)
*A61B 5/0255* (2006.01)
*A61B 5/021* (2006.01)

(56) References Cited

U.S. PATENT DOCUMENTS

| | | | |
|---|---|---|---|
| 10,398,381 B1* | 9/2019 | Heneghan | A61B 5/6814 |
| 2019/0038149 A1* | 2/2019 | Gopalakrishnan | A61B 5/681 |

* cited by examiner

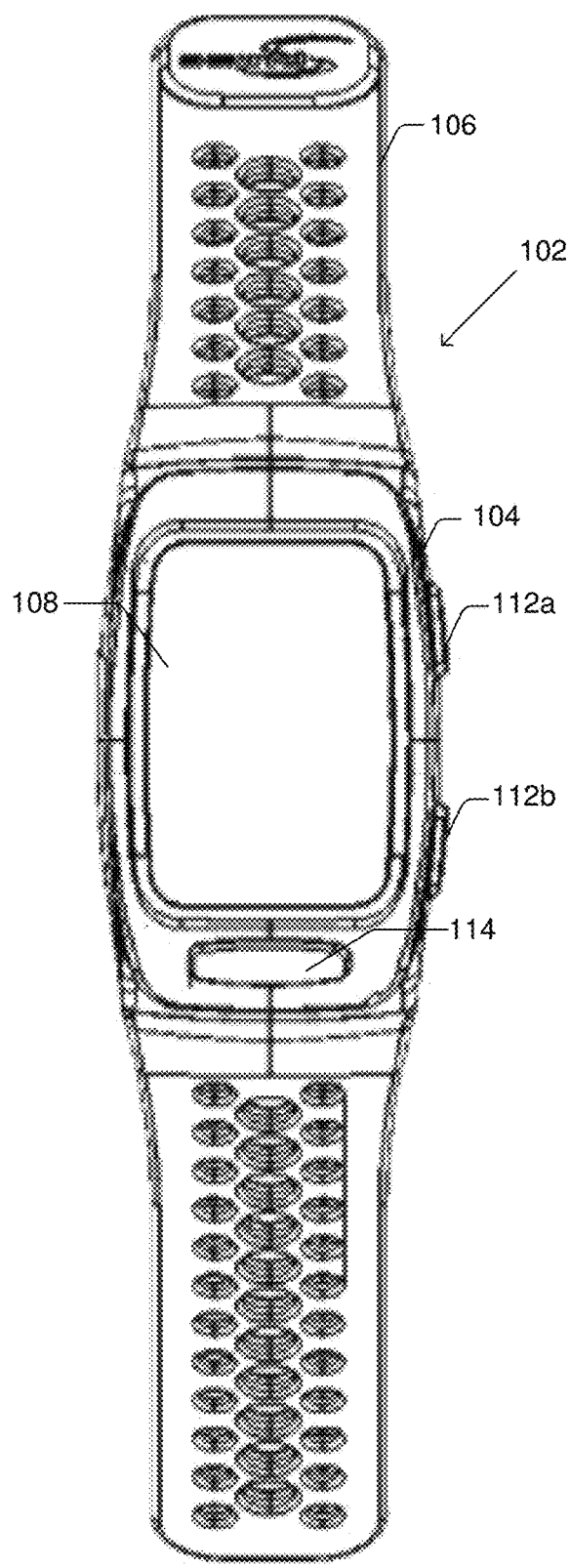 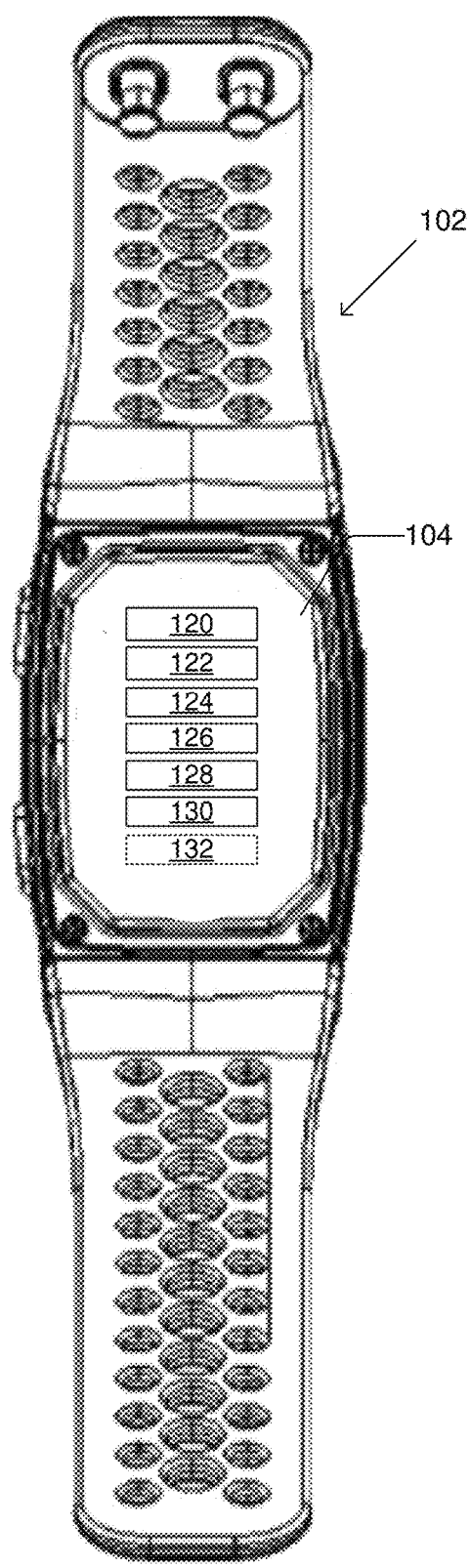
FIG. 1A                    FIG. 1B

ARRHYTHMIA MONITORING USING PHOTOPLETHYSMOGRAPHY

PRIORITY CLAIM

This application claims priority to U.S. Provisional Patent Application No. 62/567,683, filed Oct. 3, 2017, which is incorporated herein by reference.

BACKGROUND

The heart is a hollow muscular organ that is the key engine of the circulatory system serving as a pump to transport blood to the body. It takes blood that has been oxygenated in the lungs and pumps it through the arterial vessels of the circulatory system to provide oxygen and nutrients to all body tissues and organs. It then takes it back it from the veins to pump the blood into the lungs to re-oxygenate it and repeat the cycle, which takes place on the order of 100,000 times per day. In a normal heart every cycle corresponds to a regular heartbeat. The heart consists of four chambers, arranged in two upper chambers, known as atria, and two lower chambers, known as ventricles. A group of cells in the upper part of the right atrium, forms a specialized tissue known as the Sinoatrial Node (SA), which is the heart's natural pacemaker. It controls the regular heart rate, by generating electrical impulses that propagate through the heart, causing the heart to pump the blood to the body. These electrical signals can be monitored and recorded through a method known as electrocardiography (EKG or ECG for short), which is commonly used in the practice of modern medicine. A typical recording of ECG activity, which is known as an electrocardiogram (ECG), is used to display the electrical activity of the heart on a beat-to-beat basis and is typically collected continuously for a period of time, so as to observe the individual beat features, as well as the consecutive beat-to-beat heart behavior. Every regular heart beat features a particular electrical pattern comprising a P-wave, a QRS complex, a T wave, and optionally a U wave.

As the heartbeat electrical pattern travels throughout the heart it triggers the regular contraction of the heart chambers as it pumps blood to the body. A departure from a normal function of the heart can occur through a condition in which the heartbeat electrical signal is irregular, known as cardiac arrhythmia, or arrhythmia for short.

Arrhythmia (also known as dysrhythmia) can manifest itself either by an irregular heart rhythm that is faster than normal (tachycardia) or slower than normal (bradycardia). It can also occur in the form of irregular patterns.

Arrhythmias are a result of problems with the heart's electrical conduction pathways. There are four general types of arrhythmias: premature beats, escape rhythms, irregular rhythms, and tachy-arrhythmias. Among all types of arrhythmias, atrial fibrillation (AF), is the most common sustained arrhythmia in Europe and US, affecting between 2 to 3% of the population.

ECG is the natural technology of choice to monitor arrhythmia, as it can measure and record the electrical signals of the heart and potential problems associated with it. Traditionally, obtaining an ECG signal requires the placement of electrodes on a human body. The clear disadvantage of monitoring for arrhythmias based on electrocardiography, however, is that an arrhythmia may not be detected from an ECG signal obtained during a brief medical examination, and it may require longer measurement periods. Alternative methods include the use of a continuous ambulatory electrocardiographic monitor, such as a Holter monitor. As with electrocardiography, the Holter monitor requires the placement of electrodes on a human chest, and can record the electrical heart activity for a typical period of 24 to 48 hours, though it can be extended for a period of 14 days. Other more recent techniques include the use of a patch that can record arrhythmias for similar periods of time such as the ZIO™ patch by iRhythm (headquartered in San Francisco, Calif., USA), which can typically track a subject for a period of two weeks. A key limitation of these systems relates to their inability to record electrical heart signals on a prolonged basis, with ease of use, immediate feedback and comfort.

SUMMARY

Certain embodiments of the present technology relate to user-wearable (e.g., wrist worn) devices, and methods for use therewith, wherein the user-wearable device includes an optical sensor including a light source and a light detector and configured to obtain a photoplethysmography (PPG) signal, and an electrocardiogram (ECG) sensor including electrodes and configured to obtain an electrocardiogram (ECG) signal. Such devices and methods can be used to monitor for one or more types of arrhythmias including atrial fibrillation (AF) based on a PPG signal obtained using the optical sensor of the user-wearable device. In accordance with certain embodiments, a method includes using the optical sensor of the user-wearable device to obtain a PPG signal for a user of the user-wearable device, and using a PPG based statistical and/or machine learning model to analyze the PPG signal obtained using the optical sensor to monitor for one or more types of arrhythmias including atrial fibrillation (AF). In response to detecting an arrhythmia based on the PPG signal obtained using the optical sensor, the method also includes initiating obtaining of an ECG signal for the user of the user-wearable device using the electrodes of the ECG sensor of the user-wearable device. The method also includes using an ECG based statistical and/or machine learning model to analyze the ECG signal obtained using the electrodes of the ECG sensor of the user-wearable device to confirm or reject the arrhythmia initially detected based on the PPG signal obtained using the optical sensor, and/or to perform arrhythmia discrimination. The user-wearable device can include one or more processors that is/are used to implement the PPG based statistical and/or machine learning model and the ECG based statistical and/or machine learning model. In accordance with certain embodiments, simultaneous with or within a short time (i.e., within a few seconds) of confirming or rejecting the detecting of the arrhythmia, a segment of the ECG signal obtained using the electrodes of the ECG sensor, or data indicative thereof, (alone, or along with a segment of the PPG signal, or data indicative thereof, concurrently obtained during the ECG recording) is stored in the memory of the user-wearable device. When a segment of a signal is stored in memory it can be said that raw data or a raw data segment is stored in memory, since what is stored can be unprocessed samples of a signal. In contrast, when information learned from a segment of a signal (e.g., pulse amplitude, pulse slope, heart rate, or heart rate variability) is stored in memory it can be said that processed data is stored in memory, since what is stored is what is learned from performing processing on the segment of the signal.

Where the user-wearable device is a wrist or arm worn device, the optical sensor (which can also be referred to as a PPG sensor) and one of the electrodes (of the ECG sensor)

can be included on a backside of a housing of the user-wearable device. This way, so long as the device is being worn, one of the electrodes of the ECG sensor is always in contact with one of the user's arms, as is the PPG sensor, which enables a PPG signal to be obtained by the device at any time. In accordance with certain embodiments, initiating obtaining of an ECG signal for the user of the user-wearable device, in response to detecting an arrhythmia based on the PPG signal obtained using the optical sensor, involves triggering a notification that instructs the user of the user-wearable device to touch another one of the electrodes of the ECG sensor of the user-wearable device (e.g., a front facing electrode) with a finger on a hand of an arm opposite an arm on which the user-wearable device is being worn. Such a notification can be a visual, auditory and/or tactile notification. In alternative embodiments, the ECG sensor need not be part of the same user-wearable device that includes the PPG sensor. In certain embodiments, such as those where an ECG sensor is strapped to a user's chest and has electrodes in contact with a user's chest, initiating obtaining of an ECG signal for the user can involve sending instructions (e.g., wirelessly) to the ECG sensor to cause the ECG sensor to obtain an ECG signal.

In accordance with certain embodiments, the method can also include updating the PPG based statistical and/or machine learning model based on a segment of the PPG signal that caused the detecting of the arrhythmia along with a segment of the ECG signal obtained in response to guidance from the PPG monitored signal, and that is used to confirm or reject the arrhythmia (if available), and/or updating the ECG based statistical and/or machine learning model based on a segment of the ECG signal, along with the corresponding PPG signal that caused the detection of the arrhythmia.

In accordance with yet other embodiments, initiating obtaining of an ECG signal may be a result of the user desiring to collect an ECG signal in response to some other trigger due to a possible arrhythmic symptom, such as dizziness, or for no specific reason, other than the simple desire to self-monitor the ECG status of the user, or upon a request by a third party such as a medic. ECG monitoring may automatically include simultaneous PPG monitoring. In such embodiments, the method can also include updating the PPG based statistical and/or machine learning model based on a segment of a PPG signal obtained simultaneously with a segment of the initiating ECG signal obtained, and/or updating the ECG based statistical and/or machine learning model based on a segment of the ECG signal, along with the corresponding PPG signal concurrently collected with the initiating ECG signal. The models may be updated based on the monitored ECG and corresponding PPG signals, responsive to whether the signals confirm or reject the presence of arrhythmia.

In accordance with certain embodiments, prior to the performing arrhythmia monitoring, a plurality of ECG signal segments that correspond to each of a normal sinus rhythm (NSR) and to each of the one or more types of arrhythmias including AF are obtained. Additionally, a plurality of PPG signal segments that correspond to each of the NSR and to each of the one or more types of arrhythmias including AF are also obtained. Further, the ECG and PPG based statistical and/or machine learning models are generated, respectively, based on the obtained ECG and PPG signal segments, which are examples of ECG and PPG data sets.

In accordance with certain embodiments, a measure of blood pressure is determined based on the PPG and ECG signals obtained, respectively, using the optical sensor and the electrodes of the user-wearable device. In such embodiments, the measure of blood pressure can also be used to confirm or reject the arrhythmia detected based on the PPG signal obtained using the optical sensor.

In accordance with other embodiments, initiating obtaining of a PPG signal for the user of the user-wearable device, would result in a PPG signal that will have a waveform that uniquely represents the physiological state of the user. Among some of the key features of the PPG waveform, is the pulse amplitude represented by the peak to trough amplitude of the PPG signal. The pulse amplitude may change with every beat, and it may also change based on various physiological changes that may be present in the user. The amplitude of the PPG signal can be impacted by stroke volume, vascular compliance and local conditions at the site of measurement. Given a similar context, however, such as monitoring PPG on a given body location at bed time, during sleep, after wake up, or under any other controlled context, the change in amplitude is expected to vary to a lesser extent. A significant change in amplitude or a gradual change in amplitude with time, however, within a similar context, may be indicative of a corresponding change in the physiological state of the individual, which may result in a change in vascular compliance. A change in blood pressure, in particular, may impact the vascular compliance. Active changes to the vascular tone, via for example sympathetic activity or the presence of various vasoactive substances may also impact the PPG pulse amplitude. Correlation between PPG pulse amplitude and blood pressure may potentially become dominant, however, under a similar context. In such embodiments, the measure of PPG amplitude, uniquely requiring PPG alone, can be a proxy (i.e., surrogate) for a blood pressure marker, which can in turn, also be used to confirm or reject the arrhythmia detected based on the PPG signal obtained using the optical sensor. It is noted that the terms proxy and surrogate are used interchangeably herein.

In accordance with yet other embodiments, initiating obtaining of a PPG signal for the user of the user-wearable device, would result in a PPG signal that will have a waveform that uniquely represents the physiological state of the user. Among other additional key features of the PPG signal waveform, is the PPG signal shape, which given a similar context, such as the monitoring of PPG on a given body location at bed time, during sleep, after wake up, or under any other controlled context, may also be used alone to serve as a proxy (i.e., surrogate) for a blood pressure marker, which can in turn, be used to confirm or reject the arrhythmia detected based on the PPG signal obtained using the optical sensor.

These additional key features of the PPG signal waveform, may further be used in combination with the PPG pulse amplitude, so as to provide a higher confidence proxy for a blood pressure marker, which can in turn, be used to also confirm or reject the arrhythmia detected based on the PPG signal obtained using the optical sensor.

A user-wearable device, according to certain embodiments of the present technology, includes an optical sensor configured to obtain a PPG signal, electrodes configured to obtain an ECG signal, and an arrhythmia detector. The arrhythmia detector, in accordance with certain embodiments, is configured to use a PPG based statistical and/or machine learning model to monitor for one or more types of arrhythmias including AF based on a PPG signal obtained using the optical sensor. The arrhythmia detector is also configured to initiate obtaining of an ECG signal for the user of the user-wearable device using the electrodes of the user-wearable device, in response to an arrhythmia being detected based on the PPG signal obtained using the optical sensor. Further, the arrhythmia detector is configured to use an ECG based statistical and/or machine learning model to analyze an ECG signal obtained using the electrodes to confirm or reject a detection of an arrhythmia based on a PPG signal obtained using the optical sensor, and/or to perform arrhythmia discrimination. The arrhythmia detector, which can be implemented using one or more processors of the user-wearable device, can also be configured to update the PPG based statistical and/or machine learning model based on a segment of the PPG signal that caused the detecting of the arrhythmia, along with a segment of the ECG signal obtained in response to guidance from the PPG monitored signal, and that is used to confirm or reject the arrhythmia (if available), and/or update the ECG based statistical and/or machine learning model based on a segment of the ECG signal, along with the corresponding PPG signal that caused the detection of the arrhythmia, and is to be confirmed, rejected, or classified.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 1A depicts a front view of a user-wearable device, according to an embodiment.

FIG. 1B depicts a rear view of the user-wearable device of FIG. 1A, according to an embodiment.

DETAILED DESCRIPTION

Figure 1C:
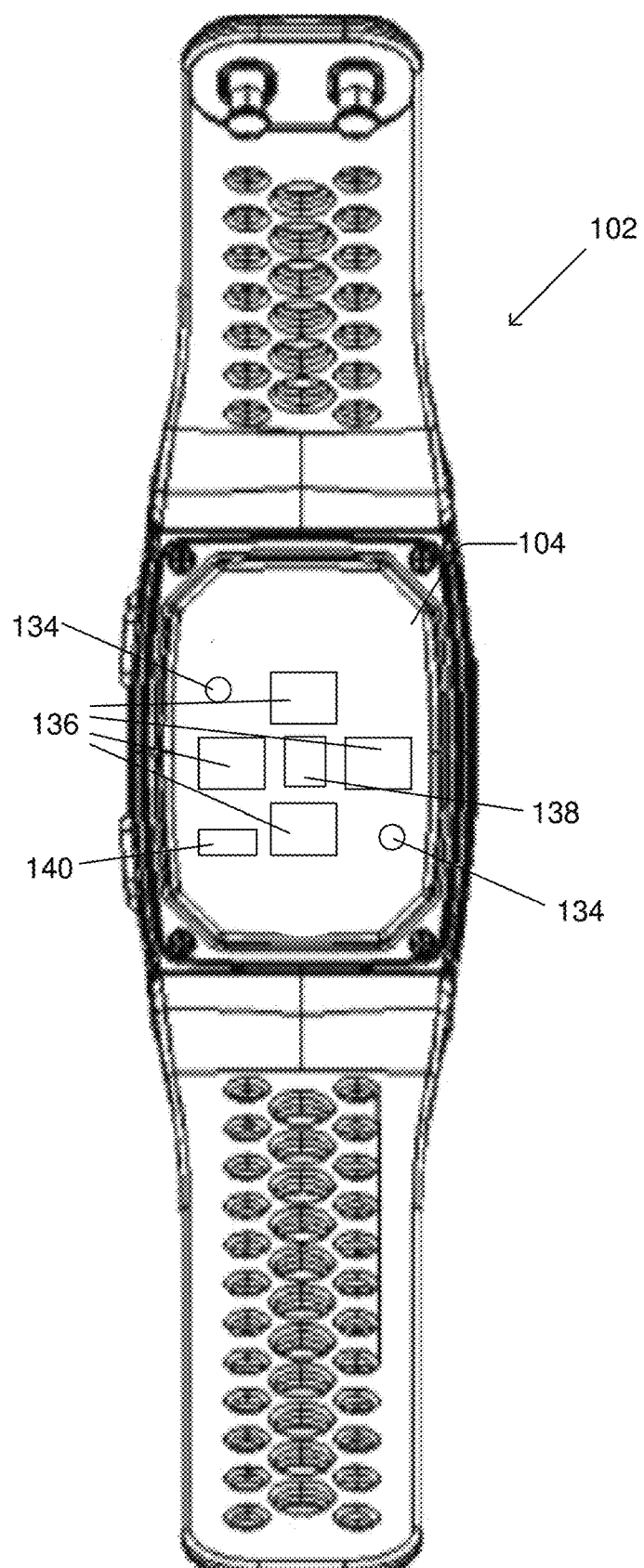
FIG. 1C depicts a specific implementation of contact sensors that are viewable from the rear or caseback of the user-wearable device of FIGS. 1A and 1B, according to an embodiment.

In the following detailed description, reference is made to the accompanying drawings that form a part hereof, and in which is shown by way of illustration of specific exemplary embodiments. It is to be understood that other embodiments may be utilized and that mechanical and electrical changes may be made. The following detailed description is, therefore, not to be taken in a limiting sense. In the description that follows, like numerals or reference designators will be used to refer to like parts or elements throughout. In addition, the first digit of a reference number identifies the drawing in which the reference number first appears.

Certain embodiments of the present technology can be used to monitor for cardiac arrhythmias based on a PPG signal obtained from a user-wearable device, which is preferably a wrist worn device that resembles a wrist watch, but is not limited thereto. Before describing specific embodiments of the present technology, it is first useful to describe an exemplary user-wearable device that can be used to obtain a PPG signal that is used to monitor for arrhythmias as well as an electrocardiogram (ECG) signal that is used to determine whether an arrhythmia detected based on a PPG signal is likely an actual arrhythmia, as well as to improve models that are used to monitor for arrhythmias based on a PPG signal in accordance with embodiments of the present technology. FIG. 1A depicts a front view of a user-wearable device 102, according to an embodiment. The user-wearable device 102 can be a standalone device which gathers and processes data and displays results to a user. Alternatively, the user-wearable device 102 can wirelessly communicate with a base station (252 in FIG. 2), which can be a mobile phone, a tablet computer, a personal data assistant (PDA), a laptop computer, a desktop computer, or some other computing device that is capable of performing wireless communication. The base station can, e.g., include a health and fitness software application and/or other applications, which can be referred to as apps. The user-wearable device 102 can upload data obtained by the device 102 to the base station, so that such data can be used by a health and fitness software application and/or other apps stored on and executed by the base station.

The user-wearable device 102 is shown as including a housing 104, which can also be referred to as a case 104. A band 106 is shown as being attached to the housing 104, wherein the band 106 can be used to strap the housing 104 to a user's wrist or arm. Where the user-wearable device 102 includes the wrist type band 106, the device 102 can also be referred to as a wrist-wearable or wrist-worn device. The band can alternatively be configured to strap the housing 104 to the user's chest so that sensors and/or electrodes (of or for use by the sensors) are in contact with the skin on the user's chest. A front side of the housing 104 is shown as including a digital display 108, which can also be referred to simply as a display. The digital display 108 can be used to show the time, date, day of the week and/or the like. The digital display 108 can also be used to display physiological metrics, such as, but not limited to, heart rate (HR), heart rate variability (HRV), as well as to provide arrhythmia alerts and/or instructions. For example, in accordance with certain embodiments of the present technology, the digital display 108 may instruct a user to touch a forward facing ECG electrode 114, after the device 102 has detected an arrhythmia based on a PPG signal, to thereby enable the device 102 to obtain an ECG signal, by itself, or along with a concurrently obtained PPG signal, that can be used to confirm or refute occurrence of the arrhythmia, can be recorded for later analysis, and can be used to collect prospective data for the device 102 to improve future arrhythmia monitoring by the device 102. Where the device 102 also monitors exercise related activities, the digital display 108 can also display activity metrics, such as, but not limited to, calories burned, steps taken and distance walked and/or run. The digital display 108 can also be used to display sleep metrics, examples of which are discussed below. These are just a few examples of the types of information that may be displayed on the digital display 108, which are not intended to be all encompassing. As the terms are used herein, the terms user, wearer and person are typically used interchangeably.

The housing 104 is further shown as including buttons 112*a*, 112*b*, which can individually be referred to as a button 112, and can collectively be referred to as the buttons 112. One of the buttons 112 can be a mode select button, while another one of the buttons 112 can be used to start and stop certain features. While the user-wearable device 102 is shown as including two buttons 112, more or less than two buttons can be included. The buttons 112 can additionally or alternatively be used for other functions. The housing 104 is further shown as including the forward facing ECG electrode 114, which was mentioned above, and is discussed in more detail below. This ECG electrode 114 can also function as an additional button. While the shapes of the housing 104 and the digital display 108 are shown as generally being rectangular, they can alternatively have other shapes, such as, but not limited to, circular or oval shapes.

In certain embodiments, the user-wearable device 102 can receive alerts from a base station (e.g., 252 in FIG. 2), or can generate its own alerts. For example, where the base station 252 is a mobile phone, the user-wearable device 102 can receive alerts from the base station, which can be displayed to the user on the display 108. For a more specific example, if a mobile phone type of base station 252 is receiving an incoming phone call, then an incoming phone call alert can be displayed on the digital display 108 of the mobile device, which may or may not include the phone number and/or identity of the caller. Other types of alerts include, e.g., arrhythmia alerts, text message alerts, social media alerts, calendar alerts, medication reminders and exercise reminders, but are not limited thereto. Still other types of alerts can inform a user that they should adjust their exposure to light, as will be described in additional detail below. Such alerts can be generated solely by the user-wearable device 102, or with the assistance of a base station (e.g., 252) with which the user-wearable device 102 wirelessly communicates. The user-wearable device 102 can inform the user of a new alert by vibrating and/or emitting an audible sound.

FIG. 1B illustrates an exemplary rear-view of the housing or case 104 of the user-wearable device 102. Referring to FIG. 1B, the backside of the housing 104, which can also be referred to as a caseback, is schematically shown as including a bioimpedance analysis (BIA) sensor, an optical sensor 122, a capacitive sensor 124, a galvanic skin resistance (GSR) sensor 126, an electrocardiogram (ECG) sensor 128 and a skin temperature sensor 130. It is also possible that the user-wearable device 102 includes less sensors than shown, more sensors than shown and/or alternative types of sensors. For example, the user-wearable device 102 can also include one or more type of motion sensor 132, which is shown in dotted line because it is likely completely encased with the housing 104.

In accordance with an embodiment, the bioimpedance analysis (BIA) sensor 120, which can include or connect to a pair of electrodes spaced apart from one another such that a person's skin can complete a circuit between the electrodes, passes a current at a single frequency, or more preferably at multiple frequencies, through a user's tissue (proximate the sensor electrodes) and measures impedance. Based on these impedance measurements, algorithms, linear regression models and/or other mathematical modeling can be used to calculate the user's body water content and/or body fat percentage.

In accordance with an embodiment, the optical sensor 122 includes both a light source and a light detector, in which case the optical sensor 122 can be used to detect proximity of an object (e.g., a user's wrist or chest) relative to the optical sensor, as well as to detect ambient light. The light source of the optical sensor 122 can include one or more light emitting diode (LED), incandescent lamp or laser diode, but is not limited thereto. While infrared (IR) light sources are often employed in optical sensors, because the human eye cannot detect IR light, the light source can alternatively produce light of other wavelengths. The light detector of the optical sensor 122 can include one or more one or more photoresistor, photodiode, phototransistor, photodarlington or avalanche photodiode, but is not limited thereto. When operating as an optical proximity sensor, the light source of the optical sensor 122 is driven to emit light. If an object (e.g., a user's wrist or chest) is within the sense region of the optical sensor 122, a large portion of the light emitted by the light source will be reflected off the object and will be incident on the light detector. The light detector generates a signal (e.g., a current) that is indicative of the intensity and/or phase of the light incident on the light detector, and thus, can be used to detect the presence of the user's wrist or chest. The optical sensor 122 may also use its light detector to operate as an ambient light detector. It is also possible that the optical sensor 122 not include a light source, in which case the optical sensor 122 can operate as an ambient light sensor, but not a proximity sensor. When operating as an ambient light sensor, the optical sensor 122 produces a signal having a magnitude that is dependent on the amount of ambient light that is incident on the optical sensor 122. It is expected that when a user is wearing the user-wearable device 102 on their wrist or chest, the light detector of the optical sensor 122 will be blocked (by the user's wrist or chest) from detecting ambient light, and thus, the signal produced at the light detector will have a very low magnitude.

In accordance with specific embodiments, the optical sensor 122 can also be used to detect heart rate (HR) and heart rate variability (HRV). More specifically, the optical sensor 122 can operate as a photoplethysmography (PPG) sensor. When the optical sensor 122 is operating as a PPG sensor, it can alternatively be referred to as a PPG sensor 122. When operating as a PPG sensor, the light source of the optical sensor 122 emits light that is reflected or backscattered by the wearer's tissue, and reflected/backscattered light is received by the light detector of the optical sensor 122. In this manner, changes in reflected light intensity are detected by the light detector, which outputs a PPG signal indicative of the changes in detected light, which are indicative of changes in blood volume. The PPG signal output by the light detector can be filtered and amplified, and can be converted to a digital signal using an analog-to-digital converter (ADC), if the PPG signal is to be analyzed in the digital domain. Each cardiac cycle in the PPG signal generally appears as a peak, thereby enabling the PPG signal to be used to detect peak-to-peak intervals (which can also be referred to as RR' intervals), which can be used to calculate heart rate (HR) and heart rate variability (HRV). It would also be possible to use a PPG signal sensed using the optical sensor 122 as a biometric signal that is used to determine whether or not to authenticate a user. In accordance with certain embodiments, the optical sensor 122 includes a light source that emits light of two different wavelengths that enables the optical sensor 122 to be used as a pulse oximeter, in which case the optical sensor 122 can non-invasively monitor the arterial oxygen saturation of a user wearing the user-wearable device 102.

In accordance with an embodiment, the capacitive sensor 124 includes or connects to an electrode that functions as one plate of a capacitor, while an object (e.g., a user's wrist or chest) that is in close proximity to the capacitive sensor 124 functions as the other plate of the capacitor. The capacitive sensor 124 can indirectly measure capacitance, and thus proximity, e.g., by adjusting the frequency of an oscillator in dependence on the proximity of an object relative to the capacitive sensor 124, or by varying the level of coupling or attenuation of an AC signal in dependence on the proximity of an object relative to the capacitive sensor 124.

The galvanic skin resistance (GSR) sensor 126, which can include or connect to a pair of electrodes spaced apart from one another such that a wearer's skin can complete a circuit between the electrodes, senses a galvanic skin resistance. The galvanic skin resistance measurement will be relatively low when a user is wearing the user-wearable device 102 on their wrist or chest and the GSR sensor 126 is in contact with the user's skin. By contrast, the galvanic skin resistance measurement will be very high when a user is not wearing the user-wearable device 102 and the GSR sensor 126 is not in contact with the user's skin. The galvanic skin resistance measurement, which can also be referred to as a galvanic skin response, may also vary based on levels of perspiration.

The ECG sensor 128 can be used to sense an ECG signal from a user that is wearing the user-wearable device 102 on their wrist or chest. If the user-wearable device 102 is worn on the user's wrist, then an ECG signal can be sensed when an electrode on the caseback of the housing 104 is in contact with the skin on the user's wrist, and the user's touches the forward facing electrode 114 using a finger on their other arm to complete a circuit. Accordingly, to obtain an ECG signal using a user-wearable device 102 being worn on one of the user's wrists (i.e., their left or right wrist), the user must know to (or be instructed to) touch the forward facing electrode 114 (or an equivalent second electrode) with a finger of the arm on which the user-wearable device is not being worn. By contrast, if the user-wearable device 102 is worn on the user's chest, then an ECG signal can be sensed between two electrodes on the back of the housing 104 that are in contact with the skin on the user's chest.

The skin temperature sensor 130 can be implemented, e.g., using a thermistor or via optical means, and can be used to sense the temperature of a user's skin, which can be used to determine an estimate for user body temperature and physiological state and wellbeing.

Depending upon implementation, heart rate (HR) and heart rate variability (HRV) can be detected based on signals obtained by the optical sensor 122 and/or the ECG sensor 128. HR and/or HRV can be automatically determined continuously, periodically or at other specified times or based on a manual user action. For example, in a free living application, HR can be determined automatically during periods of interest, such as when a significant amount of activity is detected.

Additional physiologic metrics can also be obtained using the sensors described herein. For example, respiration rate can be determined from a PPG signal obtained using the optical sensor 122 and/or from the ECG signal determined using the ECG sensor 128. For another example, blood pressure can be determined from PPG and ECG signals by determining a metric of pulse wave velocity (PWV) and/or pulse transit time (PTT) and converting the metric(s) of PWV and/or PTT to a metric of blood pressure. More specifically, a metric of PWV and/or PTT can be computed by determining a time from a specific feature (e.g., an R-wave) of an obtained ECG signal to a specific feature (e.g., a maximum upward slope, a maximum peak or a dicrotic notch) of a simultaneously obtained PPG signal. An equation can then be used to convert the metric of PWV and/or PTT to a metric of blood pressure.

In accordance with an embodiment the motion sensor 132 is an accelerometer. The accelerometer can be a three-axis accelerometer, which is also known as a three-dimensional (3D) accelerometer, but is not limited thereto. The accelerometer may provide an analog output signal representing acceleration in one or more directions. For example, the accelerometer can provide a measure of acceleration with respect to x, y and z axes. The motion sensor 132 can alternatively be a gyrometer, which provides a measure of angular velocity with respect to x, y and z axes. It is also possible that the motion sensor 132 is an inclinometer, which provides a measure of pitch, roll and yaw that correspond to rotation angles around x, y and z axes. It is also possible the user wearable device 102 includes multiple different types of motion sensors, some examples of which were just described. Depending upon the type(s) of motion sensor(s) used, such a sensor can be used to detect the posture of a portion of a user's body (e.g., a wrist or chest) on which the user-wearable device 102 is being worn. Additionally, or alternatively, the motion sensor 132 can be used to produce an actigraphy signal.

In the specific embodiments illustrated in FIGS. 1A, 1B and 1C the user-wearable device 102 is intended to be worn on a wrist, and thus, can be referred to as a wrist wearable device 102. FIG. 1C illustrates a rear-view of the housing or case 104 of the user-wearable device 102 according to a specific embodiment. Referring to FIG. 1C, the back of the housing or case 104, which can also be referred to as the caseback, is shown as including two electrodes or electrode contacts 134 that are spaced apart from one another, four light emitting devices 136, a light detecting device 138, and a metal temperature sensor contact 140.

In accordance with an embodiment, the light emitting devices 136 and the light detecting device 138 are components of the optical sensor 122 that was discussed above. The optical sensor 122 can alternatively include as few as one light emitting device, two or three light emitting devices, or more than four light emitting device. The light emitting devices may all be of the same color, or multiple colors, depending on the one or more physiological parameter(s) being monitored, e.g., blood volume, oxygenation level, and/or other parameters. It is also possible that the optical sensor 122 includes multiple light detecting devices 138. The light emitting device(s) and light detecting device(s) of the optical sensor 122 are likely covered by light transmissive windows that protect the light emitting device(s) and light detecting device(s).

The two electrodes 134 can be used for the BIA sensor 120, the capacitive sensor 124, the GSR sensor 126 and/or the ECG sensor 128. For example, switches (not shown) can be used to selectively connect the electrodes 134 to various different electrical circuits within the housing 104 so that they can selectively function as parts of different types of sensors. More specifically, such switches can be selectively connected to the two electrodes 134 to either BIA sensor circuitry, capacitive sensor circuitry, GSR sensor circuitry or ECG sensor circuitry. Where electrode(s) that are used by the BIA sensor 120, the capacitive sensor 124, the GSR sensor 126 and/or the ECG sensor 128 are in contact with the user's skin, such sensors are considered to be in contact with the user's skin.

Figure 2:
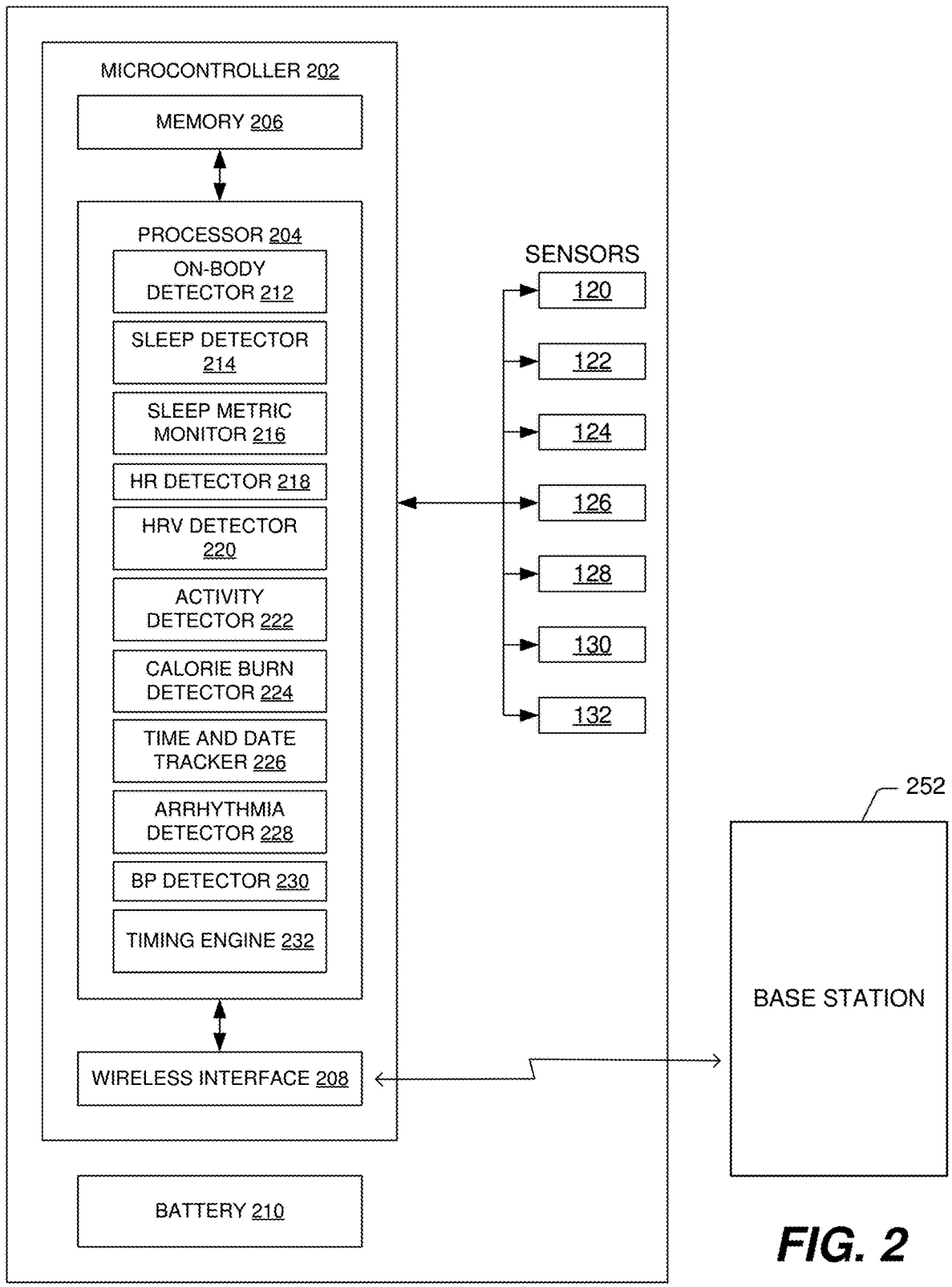
FIG. 2 depicts a high level block diagram of electrical components of the user-wearable device introduced in FIGS. 1A, 1B and 1C, according to an embodiment.

Each of the aforementioned sensors 122, 124, 126, 128, 130, 132 can include or have associated analog signal processing circuitry to amplify and/or filter raw signals produced by the sensors. It is also noted that analog signals produced using the aforementioned sensors 122, 124, 126, 128, 130 and 132 can be converted to digital signals using one or more digital to analog converters (ADCs), as is known in the art. The analog or digital signals produced using these sensors can be subject to time domain processing, or can be converted to the frequency domain (e.g., using a Fast Fourier Transform or Discrete Fourier Transform) and subjected to frequency domain processing. Such time domain processing, frequency domain conversion and/or frequency domain processing can be performed by a processor (e.g., 204), or by some other circuitry. FIG. 2 depicts an example block diagram of electrical components of the user-wearable device 102, according to an embodiment. Referring to FIG. 2, the user-wearable device 102 is shown as including a microcontroller 202 that includes a processor 204, memory 206 and a wireless interface 208. It is also possible that the memory 206 and wireless interface 208, or portions thereof, are external the microcontroller 202. The microcontroller 202 is shown as receiving signals from each of the aforementioned sensors 122, 124, 126, 128, 130 and 132. The user-wearable device 102 is also shown as including a battery 210 that is used to power the various components of the device 102. While not specifically shown, the user-wearable device 102 can also include one or more voltage regulators that are used to step-up and or step-down the voltage provided by the battery 210 to appropriate levels to power the various components of the device 102.

Each of the aforementioned sensors 120, 122, 124, 126, 128, 130, 132 can also include its own circuitry to obtain signals of interest and/or information indicative thereof. For example, the BIA sensor 120 can include circuitry that enables impedance to be measured between a pair of electrodes in contact with a user's skin at one or more frequencies. The optical sensor 122 can include circuitry that selectively drives the light source of the optical sensor 122 and circuitry that amplifies and/or filters a signal produced by the light detector of the optical sensor 122, and/or converts a current signal produced by the light detector to a voltage signal. The GSR sensor 126 can include circuitry that senses a galvanic skin resistance between a pair of electrode in contact with a user's skin. For another example, the ECG sensor 128 can include circuitry that enables an ECG signal to be sensed between a pair of electrodes in contact with a user's skin. Each of the sensors that requires that one or more electrodes be in contact with a user's skin can include or be coupled to electrodes that are dedicated to the sensor. Alternatively, two or more of the sensors that require one or more electrodes be in contact with a user's skin can share common electrodes, e.g., using switches that selectively connect electrodes to appropriate sensor circuitry in a time divisional multiplexed manner. For a more specific example, there can be a total of two electrodes (e.g., 134) on the backside of the housing 104 that contact a user's skin when the device 102 is being worn by the user. Where a sensor only requires a single electrode on the backside of the housing 104, one of the two electrodes can be used, or the two electrodes can be electrically coupled together to function as a single electrode having a larger surface area than an individual electrode. Additionally, where the battery (e.g., 210) of the device is a rechargeable battery, the same two electrodes on the backside of the housing 104 can also be selectively used to charge the battery.

The wireless interface 208 can wireless communicate with a base station (e.g., 252), which as mentioned above, can be a mobile phone, a tablet computer, a PDA, a laptop computer, a desktop computer, or some other computing device that is capable of performing wireless communication. The wireless interface 208, and more generally the user wearable device 102, can communicate with a base station 252 using various different protocols and technologies, such as, but not limited to, Bluetooth™, Wi-Fi, ZigBee or ultra-wideband (UWB) communication. In accordance with an embodiment, the wireless interface 208 comprises telemetry circuitry that include a radio frequency (RF) transceiver electrically connected to an antenna (not shown), e.g., by a coaxial cable or other transmission line. Such an RF transceiver can include, e.g., any well-known circuitry for transmitting and receiving RF signals via an antenna to and from an RF transceiver of a base station 252.

The user-wearable device 102 is shown as including various detectors or trackers, including an on-body detector 212, a sleep detector 214, a sleep metric detector 216, a heart rate (HR) detector 218, a heart rate variability (HRV) detector 220, an activity detector 222, a calorie burn detector 224, a time and date tracker 226, an arrhythmia detector 228, and a blood pressure (BP) detector 230. The various detectors and trackers may communicate with one another, as will be explained below. Each of these detectors and trackers 212, 214, 216, 218, 220, 222, 224, 226, 228 and 230 can be implemented using software, firmware and/or hardware. It is also possible that some of these detectors and trackers are implemented using software and/or firmware, with others implemented using hardware. Other variations are also possible. In accordance with a specific embodiments, each of these detectors or trackers 212, 214, 216, 218, 220, 222, 224, 226, 228 and 230 is implemented using software and/or firmware code that is stored in the memory 206 and is executed by the processor 204. The user-wearable device 102 is also shown as including a timing engine 232, which can similarly be implemented using software and/or firmware code that is stored in the memory 206 and is executed by the processor 204. The memory 206 is an example of a tangible computer-readable storage apparatus or memory having computer-readable software embodied thereon for programming a processor (e.g., 204) to perform a method. For example, non-volatile memory can be used. Volatile memory such as a working memory of the processor 204 can also be used. The computer-readable storage apparatus may be non-transitory and exclude a propagating signal.

The on-body detector 212 uses signals and/or data obtained from one or more of the above described sensors to determine whether the user-wearable device 102 is being worn by a user. For example, the on-body detector 212 can use signals and/or data obtained from the optical sensor 122, the GSR sensor 126, the temperature sensor 130 and/or the motion sensor 132 to determine whether the user-wearable device 102 is being worn by a user. Where the user-wearable device has the form factor of a wrist-watch, e.g., as shown in FIGS. 1A and 1B, the on-body detector 212 may be referred to as a wrist-off detector or a wrist-on detector. The on-body detector 212 can be used to selective operate the device 102 in a low power mode when the on-body detector 212 detects that the device 102 is not being worn by a user. Additional details of the on-body detector 212 are described in U.S. Pat. No. 9,442,523, titled "User-Wearable Devices with Power Conserving Features."

The sleep detector 214 uses signals and/or data obtained from one or more of the above described sensors to determine whether a user, who is wearing the user-wearable device 102, is sleeping. For example, signals and/or data obtained using the motion sensor 132 can be used to determine when a user is sleeping. This is because people typically move around less when sleeping compared to when awake. Additionally, if the user's arm posture can be detected from the motion sensor 132, then information about arm posture can also be used to detect whether or not a user is sleeping. The sleep detector 214 can also be used to detect when a user, who is wearing the user-wearable device 102, wakes up, as well as when the user is awake.

The sleep metric detector 216 uses signals and/or data obtained from one or more of the above described sensors and/or other detectors and trackers to quantify metrics of sleep, such as total sleep time, sleep efficiency, number of awakenings, and estimates of the length or percentage of time within different sleep states, including, for example, rapid eye movement (REM) and non-REM states. The sleep metric detector 216 can, for example, use signals and/or data obtained from the motion sensor 132 and/or from the HR detector 218 to distinguish between the onset of sleep, non-REM sleep, REM sleep and the user waking from sleep. One or more quality metric of the user's sleep can then be determined based on an amount of time a user spent in the different phases of sleep. Such quality metrics can be displayed on the digital display 108 and/or uploaded to a base station (e.g., 252) for further analysis.

The HR detector 218 can use signals and/or data obtained from the PPG sensor 122 to detect HR. For example, the optical sensor 222 can be used to obtain a PPG signal from which peak-to-peak intervals can be detected, which can also be referred to as beat-to-beat intervals. The beat-to-beat intervals, which are intervals between heart beats, can be converted to HR using the equation HR=(1/beat-to-beat interval)*60, with beat-to-beat interval expressed in seconds and HR expressed in beats-per-minute (bpm). Thus, if the beat-to-beat interval=1 sec, then HR=60 bpm; or if the beat-to-beat interval=0.6 sec, then HR=100 bpm. The user's HR can be displayed on the digital display 108 and/or uploaded to a base station (e.g., 252) for further analysis. The user's HR can also be provided to the HRV detector 220 and the arrhythmia detector 228, so that the user's HR can be used to determine HRV and/or detect an arrhythmia.

The HRV detector 220 can use signals and/or data obtained from the optical sensor 122 to detect HRV. For example, in the same manner as was explained above, beat-to-beat intervals can be determined from a PPG signal obtained using the PPG sensor 122. HRV can be determined by calculating a measure of variance, such as, but not limited to, the standard deviation (SD), the root mean square of successive differences (RMSSD), or the standard deviation of successive differences (SDSD) of a plurality of consecutive beat-to-beat intervals. Alternatively, or additionally, an obtained PPG signal can be converted from the time domain to the frequency domain, and HRV can be determined using well known frequency domain techniques. The user's HRV can be displayed on the digital display 108, provided to the arrhythmia detector 228, and/or uploaded to a base station (e.g., 252) for further analysis.

The activity detector 222 can determine a type and amount of activity of a user based on information such as, but not limited to, motion data obtained using the motion sensor 132, heart rate as determined by the HR detector 218, skin temperature as determined by the skin temperature sensor 130, and time of day. The activity detector 222 can use motion data, obtained using the motion sensor 132, to determine the number of steps that a user has taken with a specified amount of time (e.g., 24 hours), as well as to determine the distance that a user has walked and/or run within a specified amount of time. Activity metrics can be displayed on the digital display 108, provided to the arrhythmia detector 228, and/or uploaded to a base station (e.g., 252) for further analysis.

The calorie burn detector 224 can determine a current calorie burn rate and an amount of calories burned over a specified amount of time based on motion data obtained using the motion sensor 132, HR as determined using the HR detector 218, and/or skin temperature as determined using the skin temperature sensor 130. A calorie burn rate and/or an amount of calories burned can be displayed on the digital display 108 and/or uploaded to a base station (e.g., 252) for further analysis.

The time and date tracker 226 can keep track of the time of day, date, and/or the like, which are typically tracked by a digital wristwatch. The time and date can be displayed on the digital display 108. Additionally, the time and date tracker 226 of the user-wearable device can be synced with a similar tracker of the base station 252. The time and date tracker 226 can provide time of day and date information to the other detectors described herein.

In accordance with certain embodiments of the present technology, the arrhythmia detector 228 can utilize a PPG based statistical model and an ECG based statistical model to detect arrhythmias in real or near real time, respectively, based on a PPG signal (obtained using the PPG sensor 122) and an ECG signal (obtained using the ECG sensor 128). More specifically, in accordance with certain embodiments, described in more detail below, a PPG based statistical model can be used to monitor for and detect an arrhythmia (including, but not limited to, AF) based on a PPG signal obtained using the PPG sensor 122, and then an ECG based statistical model can be used to confirm or reject the detection of the arrhythmia based on an ECG signal obtained by the ECG sensor 128 (after the arrhythmia is initially detected based on the PPG signal). Additionally, or alternatively, the ECG based model, alone or together with the PPG based model, can be used to perform arrhythmia discrimination. Additional details of such embodiments are provided below.

The blood pressure (BP) detector 230 can determine a measure of blood pressure for a user wearing the user-wearable device 102 by determining a metric of pulse wave velocity (PWV) and/or pulse transit time (PTT) from PPG and ECG signals (obtained, respectively, using the PPG sensor 122 and the ECG sensor 128), and converting the metric(s) of PWV and/or PTT to a measure of blood pressure. For example, a metric of PWV and/or PTT can be computed by determining a time from a specific feature (e.g., an R-wave) of an obtained ECG signal to a specific feature (e.g., a maximum upward slope, a maximum peak or a dicrotic notch) of an obtained PPG signal, and using an equation to convert the metric of PWV and/or PTT to a metric of blood pressure. A metric of PWV and/or a metric of PTT can be used as a surrogate of blood pressure. That is, such metrics can be used to help detect an arrhythmia, help confirm or reject an arrhythmia detection, and/or help perform arrhythmia discrimination without converting the metric of PWV and/or the metric of PTT to a metric of blood pressure using an equation or the like.

Instead of (or in addition to) determining a metric of blood pressure based on PWV and/or PTT (as determined based on both PPG and ECG signals), it would also be possible for the BP detector 230 to determine a proxy (i.e., surrogate) for BP based solely on a PPG signal. Among some of the key features of the PPG waveform, is the pulse amplitude represented by the peak to trough amplitude (i.e., max to min) of the PPG signal. The pulse amplitude may change with every beat, and it may also change based on various physiological changes that may be present in the user. The amplitude of the PPG signal can be impacted by stroke volume, vascular compliance and local conditions at the site of measurement. Given a similar context, however, such as monitoring of a PPG signal obtained from a PPG sensor on a given body location at bed time, during sleep, after wake up, or under any other controlled context, the change in amplitude is expected to vary to a lesser extent. A significant change in amplitude or a gradual change in amplitude with time, however, within a similar context, may be indicative of a corresponding change in the physiological state of the individual, which may result in a change in vascular compliance. A change in blood pressure, in particular, may impact the vascular compliance. Active changes to the vascular tone, via for example sympathetic activity or the presence of various vasoactive substances may also impact the PPG pulse amplitude. Correlation between PPG pulse amplitude and blood pressure may potentially become dominant, however, under a similar context. In such embodiments, the measure of PPG amplitude, uniquely requiring PPG alone, can be a proxy (i.e., surrogate) for a blood pressure marker, which can in turn, also be used by the arrhythmia detector 228 to confirm or reject the arrhythmia detected based on the PPG signal obtained using the optical sensor.

The timing engine 232 can determine when PPG and/or ECG signals are to be obtained, as well as when to cause the arrhythmia detector 228 to monitor for one or more types of arrhythmias including AF. The timing engine 232 can make such determinations, e.g., based on information obtained from one or more motions sensor(s), and/or signals or data obtained from other sensors. In accordance with certain embodiments of the present technology, in order to conserve energy and thereby extend battery life (between battery replacement or recharging), the device 102 (and more particularly, the timing engine 232) monitors for user movement and/or signal noise and suspends arrhythmia monitoring when the user movement exceeds a corresponding threshold and/or the signal noise exceeds a corresponding threshold. Suspending arrhythmia monitoring during excessive user movement and/or excessive signal noise may also be beneficial because arrhythmia monitoring under such conditions would likely be inaccurate. Arrhythmia monitoring can be suspended by temporarily disabling the arrhythmia detector 228. Additionally, or alternatively, arrhythmia monitoring can be suspended by temporarily disabling the optical sensor 122, as well as by temporarily disabling the ECG sensor 128. The period of time for which certain component(s) is/are temporarily disabled can be a predetermined period of time (e.g., one, two or five minutes, but not limited thereto), or can be based on whether the user movement and/or signal noise is still being detected. User movement can be detected using one or more motion sensor(s) 132, which as noted above can be an accelerometer, a gyrometer, and/or the like. Signal noise can be detected, e.g., by determining the signal-to-noise ratio (SNR) of a PPG signal obtained using the optical sensor 122. In an embodiment where arrhythmia monitoring is temporarily disabled for a predetermined period of time, such as two minutes, after the predetermined period of time has elapsed, user movement and/or signal noise can again be analyzed to determine whether arrhythmia monitoring should again be temporarily disabled, or whether arrhythmia monitoring should be resumed. Such embodiments provide for intelligent data collection, by reducing and preferably minimizing collecting data (used for monitoring for an arrhythmia) that would otherwise be corrupted due to motion artifacts and/or other types of signal noise.

The uniqueness not just of the PPG, ECG and combined ECG/PPG signal patterns for every individual, but the nature of the patterns themselves can be used to establish and potentially confirm the presence or absence of an arrhythmic event. An arrhythmia, however, may develop over time. Atrial fibrillation (AF), the most common cardiac tachyarrhythmia in the United States of America and the world, for example, may be classified into four stages, and progress through these stages, worsening the health of the individual. An episode of AF is defined as an event lasting over thirty seconds in duration. The first stage, known as paroxysmal AF, refers to events that terminate within a seven day period. The second stage, known as persistent AF, refers to events that lasts over seven days and under a year. The third stage, known as longstanding persistent AF, refers to uninterrupted AF that lasts for over a year. The last stage, known as permanent AF, refers to the event staying permanently, reflecting no intention or ability to seek treatment. The longer one individual is in one of these stages, the more damage the heart tissue may endure. Over time, heart tissue scarring (myocardial fibrosis) may result. It is thus beneficial to monitor and detect early stages of AF, such as the paroxysmal stage.

In accordance with certain embodiments of the present technology, the timing engine 232 provides for frequent monitoring of PPG signals along with guided ECG signal monitoring to improve the capability of early arrhythmia detection, if present. Using the unique patterns of both PPG and ECG (concurrent or within a short time frame around an arrhythmic or possibly arrhythmic PPG event), as well as the combined PPG/ECG pattern, the frequency of PPG and/or ECG monitoring may be adjusted though a timing algorithm. Thus, responsive to the likelihood of an inferred and or confirmed arrhythmic pattern, the monitoring timing algorithm, in combination with the arrhythmia statistic/machine learning analytical modules, can prescribe a preferred monitoring timing protocol to increase (and preferably optimize) early detection of an arrhythmia event, while reducing (and preferably minimizing) the frequency of monitoring when there are no arrhythmic events, so as to manage power consumption of a user-wearable device (e.g., 102). Usability and functionality of the user-wearable device will benefit from a right balance of this timing algorithm.

The user-wearable device 102 can include less modules than shown in FIG. 2, more modules than shown and/or alternative types of modules. For example, the user-wearable device 102 can also include a body water content module and/or a body fat content module that calculates the user's body water content and/or body fat percentage based on measurements obtained using the BIA sensor 120. For another example, the user-wearable device 102 can include a stress module that estimates a user's stress level based on measures obtained using the GSR sensor 126, the ECG sensor 128 and/or the skin temperature sensor 130. These are just a few examples of other types of modules or detectors that can be included within user-wearable device 102, which are not intended to be all encompassing.

Figure 3:
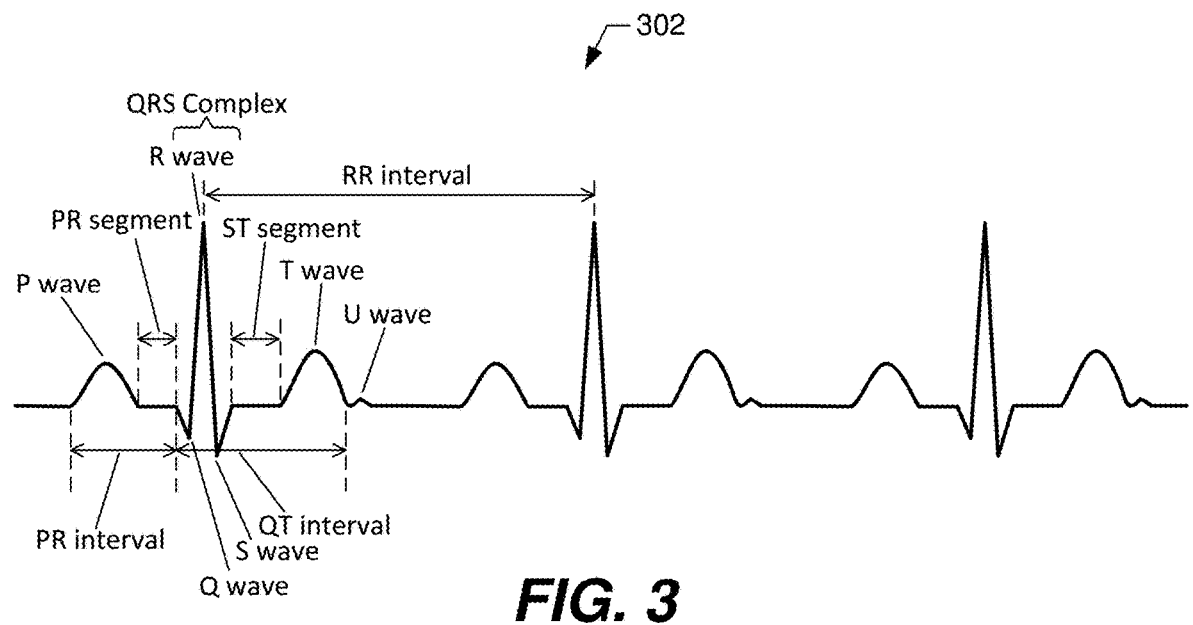
FIG. 3 is an idealized drawing of a portion of an electrocardiogram (ECG) signal, which can also be referred to as an ECG waveform.

FIG. 3 is an idealized drawing of a portion of an ECG signal 302 (which can also be referred to as an ECG waveform 302) that can be obtained using the ECG sensor 128, and more generally, using electrodes (e.g., 134 and 114). Referring to the ECG signal 302, each cycle of the signal 302 is shown as including a P wave, a QRS complex (including Q, R and S waves), a T wave and a U wave. The P wave is caused by depolarization of the atria. This is followed by an atrial contraction, during which expulsion of blood from the atrium results in further filling of the ventricle. Ventricular depolarization, indicated by the QRS complex, initiates contraction of the ventricles resulting in a rise in ventricular pressure until it exceeds the pulmonary and aortic diastolic blood pressures to result in forward flow as the blood is ejected from the ventricles. The Q, R, and S waves occur in rapid succession, and reflect a single event, and thus are usually considered together as the QRS complex. The Q wave is any downward deflection after the P wave. An R wave follows as an upward deflection, and the S wave is any downward deflection after the R wave. Ventricular repolarization occurs thereafter, as indicated by the T wave and this is associated with the onset of ventricular relaxation in which forward flow stops from the ventricles into the aorta and pulmonary arteries. Thereafter, the pressure in the ventricles falls below that in the atria at which time the mitral and tricuspid valves open to begin to passively fill the ventricles during diastole. Also shown in the exemplary ECG signal 302 is a U wave, which may not always be observed as a result of its small size, and which is thought to represent repolarization of the Purkinje fibers.

Also shown in FIG. 3 are various different intervals and segments that can be measured from an ECG signal, such as the ECG signal 302. These various intervals and segments are examples of features of an ECG signal. These include the PR interval, the QT interval, the RR interval, the PR segment, and the ST segment. The PR interval, which is sometimes referred to as the PQ interval, is the period that extends from the beginning of the P wave (the onset of atrial depolarization) until the beginning of the QRS complex (the onset of ventricular depolarization), and is normally between about 120 and 200 milliseconds (ms) in duration. The length and/or variability of the PR interval can be used to monitor for certain medical conditions, such as, but not limited to, heart block and pericarditis. The QT interval, which is the period that extends from the beginning of the Q wave until the end of the T wave, represents electrical depolarization and repolarization of the ventricles. A lengthened QT interval is a marker for the potential of ventricular tachyarrhythmias like torsades de pointes and a risk factor for sudden death. The RR interval is the period between R waves, or more generally, between QRS complexes, and is indicative of the heart rate (HR). For example, HR in beats per minute (bpm) can be determined by measuring a plurality of RR intervals, calculating an average RR interval, and dividing the number sixty (60) by the average RR interval. RR intervals can also be used to measure heart rate variability (HRV), which is the physiological phenomenon of variation in the time interval between heartbeats, which has been shown to be predictor of mortality after myocardial infarction. Additionally, a low HRV is believed to be an indicator of other conditions, such as congestive heart failure and diabetic neuropathy. The PR segment is the period that extends from the end of the P wave to the beginning of the QRS complex. PR segment abnormalities can be indicative of pericarditis or atrial ischemia. The ST segment is the period that extends from the end of the S wave (or the end of the QRS complex) to the beginning of the T wave, and is normally between about 80 and 120 ms in duration. A normal ST segment has a slight upward concavity. A flat, downsloping, or depressed ST segments, may indicate coronary ischemia. ST elevation may indicate transmural myocardial infarction. ST depression may be associated with subendocardial myocardial infarction, hypokalemia, or *digitalis* toxicity.

Figure 4:
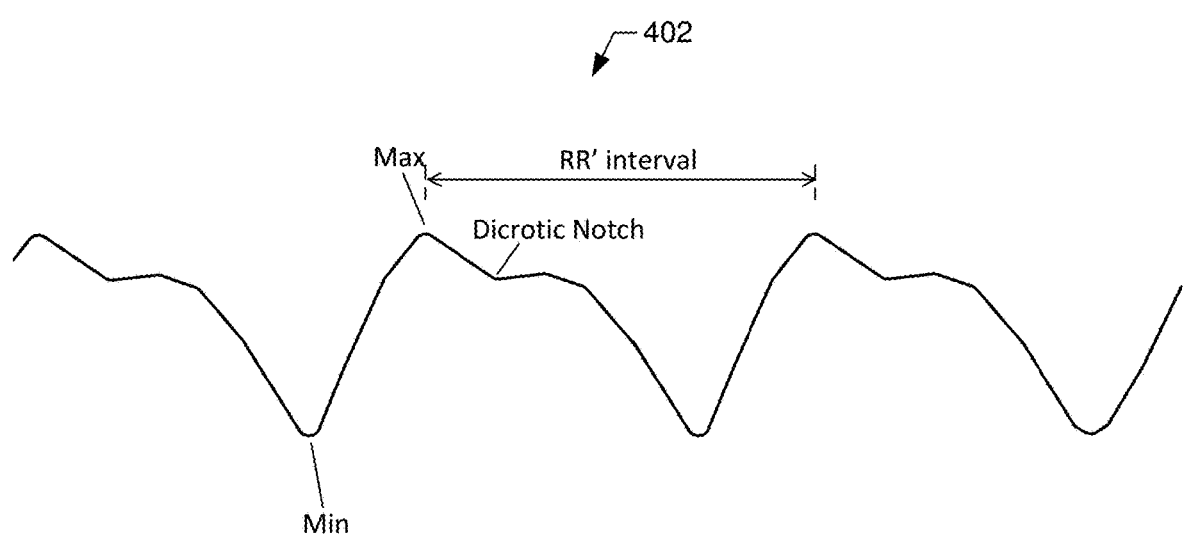
FIG. 4 is an idealized drawing of a portion of a photoplethysmography (PPG) signal, which can also be referred to as a PPG waveform.

FIG. 4 is an idealized drawing of a portion of a PPG signal 402, which can also be referred to as a PPG waveform, that can be obtained using the optical sensor 122. The optical sensor 122, when used to obtain a PPG signal, can also be referred to as a PPG sensor 122, as noted above. Each cycle of the PPG signal 402 is shown as including a minimum (min), a maximum (max), and a dicrotic notch that follows the max. However, it should be noted that the dicrotic notch may sometimes not be identifiable. The portion of the PPG waveform from a minimum to a following maximum shall also be referred to herein as the initial portion of the PPG waveform. The portion of the PPG waveform from a maximum to the following minimum shall be referred to as the terminal portion of the PPG waveform. The dicrotic notch, which is located in the terminal portion of the PPG waveform, is the first local minimum following a maximum in the PPG waveform.

Ventricular depolarization occurs at the beginning of systole, which substantially coincides with the end of diastole. The maximum peak amplitude of the PPG signal 402 occurs when a mechanical pulse resulting from the ventricular depolarization is detected by the PPG sensor, which is a distance from a location in the person's heart where the pulse originated. More specifically, the maximum (also referred to as peak) of the PPG signal 402 occurs at a time after the peak in the arterial blood pressure in the aorta at the level of the left ventricular outflow tract (note that this is representative of the time of peak pressure in the region illuminated by the PPG sensor). This is because the peak in the PPG signal 402 is indicative of the peak wave in arterial blood pressure generated by the person's heart, as detected by a PPG sensor located a distance from the person's heart. For example, if the PPG sensor is located adjacent to a person's wrist, it may take a pulse wave (as detected from ECG electrodes) on the order of about 200-250 ms to travel from the person's heart to the PPG sensor. Stated another way, a few hundreds of milliseconds after the QRS complex in an ECG signal, the PPG amplitude reaches a minimum and then starts to increase. This is due to the increasing blood volume in the arterioles as the systolic pulse reaches the periphery. The delay is influenced by the distance that the PPG sensor is placed from the heart. It requires approximately 100 ms for the amplitude of the waveform to reach its maximum. The excursion from minimum to maximum represents the arterial pulse amplitude. During diastole, the recoil of the elastic arterial vessels continues to force blood through the capillaries, so that blood flows through the capillary bed throughout the entire cardiac cycle.

In accordance with embodiments of the present technology, various features of a PPG signal, such as the PPG signal 402, can be measured and used to monitor for cardiac arrhythmias. Exemplary features of a PPG signal can include an average peak to peak interval and a peak to peak interval variability. The peak to peak interval of a PPG signal is the period between peaks (maximums) in a PPG waveform, and is indicative of the heart rate (HR), as is the RR interval that can be obtained from an ECG signal, as was explained above. In other words, there is a high correlation between the peak to peak interval of a PPG signal and the RR interval of an ECG signals, and thus, the peak to peak interval of a PPG signal can also be referred to as the RR' interval (pronounced the "RR prime interval"). HR in beats per minute (bpm) can be determined by measuring a plurality of RR' intervals, calculating an average RR' interval, and dividing the number sixty (60) by the average RR' interval. RR' intervals can also be used to measure heart peak to peak interval variability, which is highly correlated with heart rate variability (HRV), which was discussed above. Besides the peak to peak interval (also referred to as the RR' interval), and the peak to peak variability, other features of a PPG signal that can be measured include, but are not limited to, maximum upward slope, maximum downward slope, the area under the curve associated with an entire PPG cycle, the area under the curve of one or more specific portions of a PPG cycle (such as from a min to a max, from a max to a min, or from a dicrotic notch to a min, but not limited thereto), maximum downward slope prior to the dicrotic notch, maximum downward slope following the dicrotic notch, and overall morphology of a PPG waveform. It would also be possible to measure frequency characteristics of a PPG signal, e.g., by using fast Fourier transform (FFT) waveform analysis. These are just a few examples of the features of a PPG signal that can be measured, which is not intended to be all encompassing.

Arrhythmia Monitoring, Detection and Confirmation or Rejection

In a normal heart, cells of the sinoatrial node (SA node) spontaneously depolarize and thereby initiate an action potential. This action potential propagates rapidly through the atria (which contract), slowly through the atrioventricular node (AV node), the atrioventricular bundle (AV bundle or His bundle) and then to the ventricles, which causes ventricular contraction. This sequence of events is known as normal sinus rhythm (NSR). Thus, in a normal heart, ventricular rhythm relies on conduction of action potentials through the AV node and AV bundle. Rhythms that do not follow the sequence of events described above are known as arrhythmias. Those that result in a heart rate slower than normal are known as bradyarrhythmias; those that result in a faster heart rate than normal are called tachyarrhythmias. Tachyarrhythmias are further classified as supraventricular tachyarrhythmias (SVTs) and ventricular tachyarrhythmia (VT). SVTs are generally characterized by abnormal rhythms that may arise in the atria or the atrioventricular node (AV node). Additionally, there are various types of different SVTs and various types of VTs that can be characterized. For example, a paroxysmal SVT can exhibit heart rates between approximately 140 beats per minute (bpm) and approximately 250 bpm. However, the most common SVTs are typically atrial flutter (AFL) and atrial fibrillation (AF). In addition, many SVTs involve the AV node, for example, AV nodal reentry tachycardia (AVNRT) where an electrical loop or circuit includes the AV node. Another type of SVT is an AV reentrant tachycardia (AVRT), where an AV reentrant circuit typically involves the AV node and an aberrant conducting bundle known as an accessory pathway that connects a ventricle to an atrium.

Atrial flutter (AFL) can result when an early beat triggers a "circus circular current" that travels in regular cycles around the atrium, pushing the atrial rate up to approximately 250 bpm to approximately 350 bpm. The atrioventricular node between the atria and ventricles will often block one of every two beats, keeping the ventricular rate at about 125 bpm to about 175 bpm. This is the pulse rate that will be felt, even though the atria are beating more rapidly. At this pace, the ventricles will usually continue to pump blood relatively effectively for many hours or even days. A person with underlying heart disease, however, may experience chest pain, faintness, or even HF as a result of the continuing increased stress on the heart muscle. In some individuals, the ventricular rate may also be slower if there is increased block of impulses in the AV node, or faster if there is little or no block.

If the cardiac impulse fails to follow a regular circuit and divides along multiple pathways, a chaos of uncoordinated beats results, producing atrial fibrillation (AF). AF commonly occurs when the atrium is enlarged (usually because of heart disease). In addition, it can occur in the absence of any apparent heart disease. In AF, the atrial rate can increase to more than 350 bpm and cause the atria to fail to pump blood effectively. Under such circumstances, the ventricular beat may also become haphazard, producing a rapid irregular pulse. Although AF may cause the heart to lose approximately 20 to 30 percent of its pumping effectiveness, the volume of blood pumped by the ventricles usually remains within the margin of safety, again because the atrioventricular node blocks out many of the chaotic beats. Hence, during AF, the ventricles may contract at a lesser rate than the atria, for example, of approximately 125 bpm to approximately 175 bpm.

Overall, SVTs are not typically immediately life threatening when compared to ventricular arrhythmias, examples of which are discussed below.

Ventricular arrhythmias, which originate in the ventricles, include ventricular tachycardia (VT) and ventricular fibrillation (VF). Ventricular arrhythmias are often associated with rapid and/or chaotic ventricular rhythms. For example, sustained VT can lead to VF. In sustained VT, consecutive impulses arise from the ventricles at a rate of 100 bpm or more. Such activity may degenerate further into disorganized electrical activity known as ventricular fibrillation (VF). In VF, disorganized action potentials can cause the myocardium to quiver rather than contract. Such chaotic quivering can greatly reduce the heart's pumping ability. Indeed, approximately two-thirds of all deaths from arrhythmia are caused by VF. A variety of conditions such as, but not limited to, hypoxia, ischemia, pharmacologic therapy (e.g., sympathomimetics), and asynchronous pacing may promote onset of ventricular arrhythmia. Further, there are various different types of VT, including, e.g., monomorphic VT and polymorphic VT, for which different types of therapy may be appropriate.

Various types of devices and algorithms have been developed to detect arrhythmias based on ECG signals. For example, implantable cardioverter defibrillators (ICDs) and/or pacemakers can continuously obtain and monitor an ECG signal for arrhythmias because such devices are attached to leads that have electrodes chronically placed on, in and/or in close proximity to a person's heart. Accordingly, with implantable devices, arrhythmia monitoring can occur for prolonged periods of time. Nevertheless, most people do not have an ICD and/or pacemaker, and there are numerous individuals not having an ICD and/or pacemaker that would benefit from long term arrhythmia monitoring. As noted above in the Background, there exist non-implanted ambulatory devices, such as a Holter monitor or the ZIO™ patch, that can be used to obtain ECG signals over relatively short periods of time, which are typically limited to about two weeks, and are not intended for long term substantially or pseudo continuous use. A key limitation of these ambulatory devices is their limited ability to record electrical heart signals on a prolonged basis, with ease of use, immediate feedback and comfort.

Wrist worn user-wearable devices, such as the device 102, can be worn for much longer periods of time than a Holter monitor or a ZIO™ patch, and are much more discrete and comfortable because they typically look and feel like a conventional wrist watch, which many if not most people are already used to wearing for extended periods of time. Further, a wrist worn user-wearable devices, such as the device 102, can include a display and/or other user interface (UI) that can provide immediate feedback to a user. One potential limitation of using a wrist worn user-wearable device, such as the device 102, to monitor for arrhythmias is that in order to obtain an ECG using a wrist worn user-wearable device, the wearer must touch an electrode on the device (e.g., the electrode 114 on the device) with a finger on the hand of the arm that is not wearing the device (to complete a circuit). For example, if a user is wearing the device 102 on their left arm (so that an electrode on the backside of the housing is in contact with the user's left wrist), then the user must touch the front facing electrode 114 (or some other accessible second electrode) with a finger on their right arm in order for the device to obtain an ECG signal. For another example, if a user is wearing the device 102 on their right arm, then the user must touch the front facing electrode 114 (or some other accessible second electrode) with a finger on their left arm in order for the device to obtain an ECG signal. Accordingly, it is not practical for a wrist worn user-wearable device, such as the device 102, to monitor for arrhythmias over a prolonged period of time based on an ECG signal, since it is not practical for a wrist worn user-wearable device to substantially or pseudo continuously obtain an ECG signal.

Wrist worn user-wearable devices, such as the device 102, which include an optical sensor (e.g., 122) capable of obtaining a PPG signal (also referred to as a PPG sensor 122), can be used to obtain a PPG signal for prolonged periods of time because there is no requirement that a user do anything other than wear the device on one of their wrists in order for the device to be capable of obtaining a PPG signal. It is relatively easy for a wrist worn user-wearable device to detect a wearer's HR based on a PPG signal. For example, a plurality of peak to peak intervals (also referred to as RR' intervals) can be measured from a PPG signal and averaged, and a user's HR (in bpm) can be determined by dividing sixty (60) by the average peak to peak interval (also referred to as the average RR' interval), as noted above. Thus, it is relatively straightforward for such a device to be used to generally detect a tachycardia (when the user's HR exceeds some specified tachycardia threshold) and a bradycardia (i.e., when the user's HR falls below some specified bradycardia threshold). Alternatively, a tachycardia can be detected when the average peak to peak interval of a PPG signal (also referred to as an average RR' interval) falls below a first threshold, and a bradycardia can be detected when the average peak to peak interval of a PPG signal (also referred to as an average RR' interval) exceeds a second threshold. However, it is not conventional for a wrist worn user-wearable device to be capable of performing arrhythmia discrimination such that the device can distinguish between different types of tachycardias, such as, but not limited to, atrial fibrillation (AF) and atrial flutter (AFL). Embodiments of the present technology, which are described in more detail below, enable arrhythmia detection and discrimination based on a PPG signal obtained from a user-wearable device, such as the device 102.

Models and Machine Learning

Certain embodiments of the present technology rely on a statistical model to detect an arrhythmia (including, but not limited to AF) based on a PPG signal, and then use an ECG signal (obtained after an arrhythmia is initially detected based on a PPG signal) and another statistical model to confirm or reject the detection of the arrhythmia based on the PPG signal. The phrase "detect an arrhythmia," as used herein, does not mean that it is known with absolute certainty that an actual arrhythmia was detected. Rather, this phrase means that an arrhythmia is believed to have been detected based on available information, such as a PPG signal or an ECG signal. Similarly, the phrase "confirm or reject the detection of the arrhythmia" also does not mean that the confirmation or rejection of a detected arrhythmia is performed with absolute certainty. Rather, where a detection of an arrhythmia is confirmed, this means that after further analysis it is still believed that the arrhythmia was detected; and where the detection of an arrhythmia is rejected, this means that after further analysis it is no longer believed that the arrhythmia was detected. Where a device is configured to distinguish between different types of arrhythmias (i.e., is configured to perform arrhythmia discrimination) based on a PPG signal, the rejection of a specific type of arrhythmia detection can also occur, e.g., where the type of arrhythmia detected based on an ECG signal (obtained after an arrhythmia is initially detected based on a PPG signal) differs from the type of arrhythmia detected based on a PPG signal. In accordance with certain embodiments, where a type of arrhythmia detected based on a PPG is not confirmed based on the ECG signal, but there is a determination based on the ECG signal that a different type of arrhythmia occurred, then the arrhythmia detected based on the ECG signal can be considered the arrhythmia that was actually detected. In other words, the ECG signal can be used to more than simply reject the arrhythmia detection, it can be used to reclassify the arrhythmia.

In accordance with certain embodiments of the present technology, an ECG based statistical model is generated and used to detect (and preferably discriminate among) arrhythmias based on ECG signals, and a PPG based statistical model is generated and used to detect (and preferably discriminate among) arrhythmias based on PPG signals. The ECG based statistical model and the PPG based statistical model can be generated by obtaining an ECG data set including numerous (e.g., 200) ECG segments and a PPG data set including numerous (e.g., 200) PPG segments corresponding to a normal sinus rhythm (NSR), and corresponding to each of a plurality of arrhythmias of potential interest, such as, but not limited to, atrial fibrillation (AF), atrial flutter (AFL), premature atrial contractions (PACs) (also known as atrial premature complexes (APC) or atrial premature beats (APB)), premature ventricular contractions (PVCs), ventricular tachycardia (VT), and/or ventricular fibrillation (VF). The ECG based statistical model can be generated based on the ECG data set including the ECG segments to identify features of ECG signals that are indicative of NSR and each of the plurality of arrhythmias of potential interest. Similarly, the PPG based statistical model can be generated based on the PPG data set including the PPG segments to identify features of PPG signals that are indicative of NSR and each of the plurality of arrhythmias of potential interest. Each such model, once generated, can essentially function as a black box that can be provided with an ECG segment (or the PPG segment) obtained from a device, and can output an indication of whether an arrhythmia is likely represented in the ECG segment (or a PPG segment), and if so, what type of arrhythmia is likely represented. Such models can be implemented using any one or combination of statistical modeling techniques, including, but not limited to, autoregressive modeling or logistic regression modeling. It would also be possible that neural networks, such as, but not limited to Probabilistic Neural Networks (PNN) or Convolutional Neural Networks (CNN) can be used to generate such models. In accordance with certain embodiments, an ECG data engine can be used to generate the ECG based statistical model based on the ECG data set, and a PPG data engine can be used to generate the PPG based statistical model based on the PPG data set. More generally, the ECG based statistical model can be trained based on the ECG data set, and the PPG based statistical model can be trained based on the PPG data set. Segments of signals (e.g., ECG or PPG signals) that are included in a data set can also be referred to as raw data since such segments are simply unprocessed samples of a signal. Data sets can also (or alternatively) include processed data, which is data indicative of what is learned from performing processing on a segment of a signal. For example, an ECG segment may be processed to determine HR, HRV, and/or the like, and HR data, HRV data, and/or the like are examples of processed data that can be included in a data set. PPG signal segments and/or ECG signal segments can be analyzed per beat, for a few consecutive beats (to detect a short term pattern), and/or over a longer set of consecutive beats (to detect a long term pattern). Additional types of data sets can be used to generate the ECG based statistical model and/or the PPG based statistical model, as discussed in further detail below. For example, such additional types of data sets can include, e.g., skin temperature signal segments, bio-impedance signal segments, galvanic skin response signal segments, and/or actigraphy signal segments, among others, corresponding to NSR, and corresponding to each of a plurality of arrhythmias of potential interest, examples of which were mentioned above. Further, ECG data can be used to help generate the PPG based statistic model, and PPG data can be used to help generate the ECG based statistical model.

Figure 5:
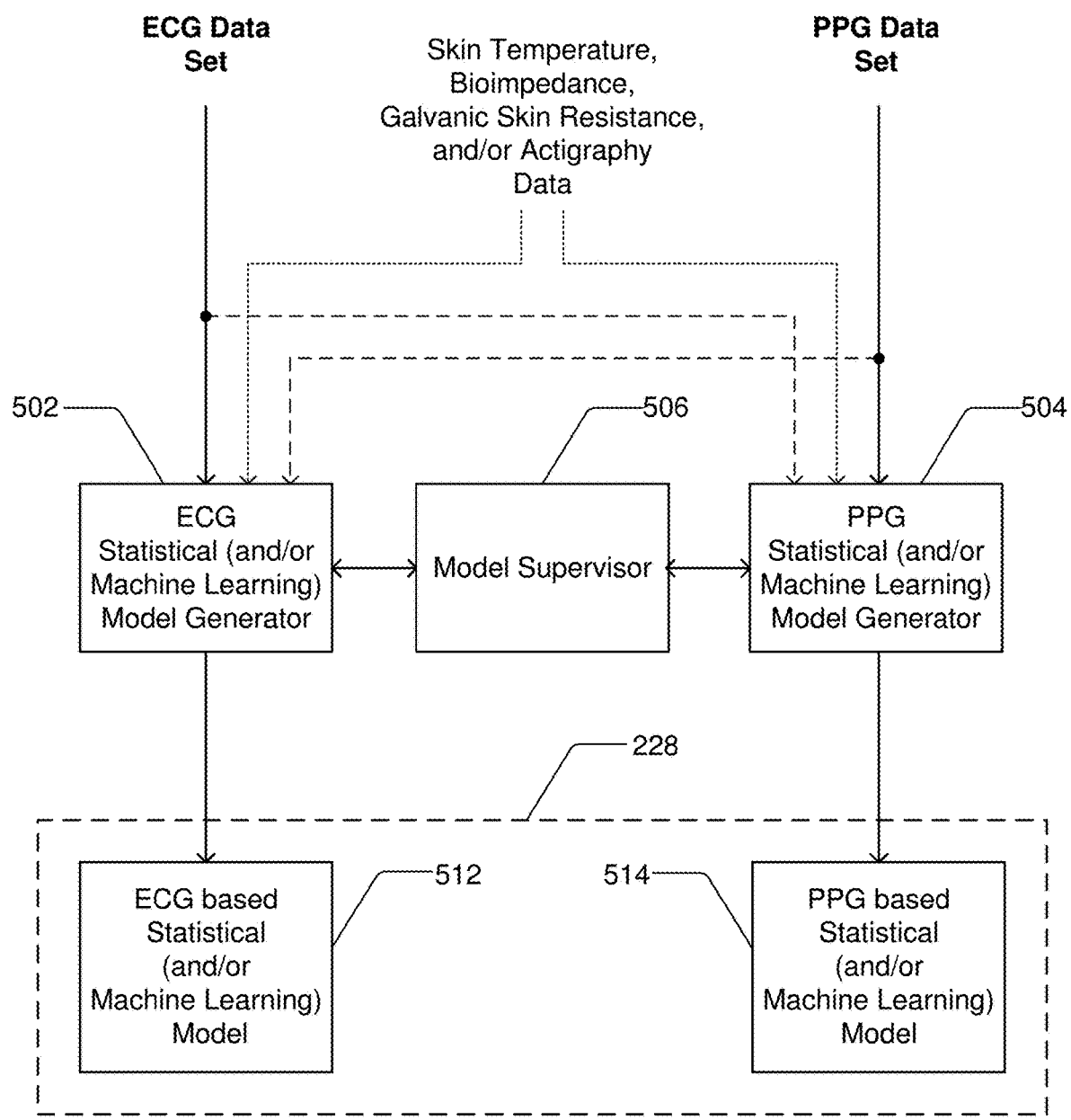
FIG. 5 is a high level block diagram that is used to explain how PPG and ECG based statistical and/or machine learning models can be generated based on PPG and ECG data sets.

Referring to FIG. 5, an ECG statistical model generator 502 can accept an ECG data set and generate an ECG based statistical model 512 in dependence thereon. Similarly, a PPG statistical model generator 504 can accept a PPG data set and generate a PPG based statistical model 514 in dependence thereon. As noted above, such an ECG data set can include numerous ECG segments corresponding to a NSR, and corresponding to each of a plurality of arrhythmias of potential interest, such as, but not limited to, AF, AFL, PACs, PVCs, VT, and/or VF. Similarly, the PPG data set can include numerous PPG segments corresponding to a NSR, and corresponding to each of a plurality of arrhythmias of potential interest, such as, but not limited to, AF, AFL, PACs, PVCs, VT, and/or VF. Also shown in FIG. 5 is a model supervisor 506 that communicates with the ECG statistical model generator 502 and the PPG statistical model generator 504 to ensure that most (if not all) arrhythmia detections produced using the ECG based statistical model 512 (generated by the ECG statistical model generator 502) and the PPG based statistical model 514 (generated by the PPG statistical model generator 504) are consistent with one another. For example, where an ECG segment (known to correspond to a specific arrhythmia) is provided to the ECG based statistical model and a corresponding PPG segment (obtained from a same person, and known to correspond to the same specific arrhythmia) is provided to the PPG based statistical model, the arrhythmia detected by the PPG based statistical model should preferably be consistent with the arrhythmia detected by the ECG based statistical model. The model supervisor 506 communicates with the model generators 502 and 504 to ensure that this is the case most (if not all) of the time. As was discussed above with reference to FIG. 2, and as shown in FIG. 5, the ECG based statistical model 512 and the PPG based statistical model 514 can be implemented by the arrhythmia detector 228 of the user-wearable device 102.

Computer readable instructions for implementing the ECG based statistical model 512 and the PPG based statistical model 514 can be stored in memory (e.g., 206), and may be implemented as software and/or firmware. Such computer readable instructions can be executed by a processor (e.g., 204) of a user-wearable device (e.g., 102) so that the PPG based statistical model 514 can be used to monitor for and detect arrhythmias in real or near-real time, and the ECG based statistical model 512 can be used to confirm or reject an arrhythmia detection by the PPG based statistical model 514.

In certain embodiments, the PPG based statistical model 514 can be used to generally detect an arrhythmia (e.g., without any specificity as to the type) based on a PPG signal, and then the ECG based statistical model 512 (after an ECG signal is obtained) can be used to perform arrhythmia discrimination (alone or in combination with the PPG based statistical model 514 and/or a BP based statistical model) to classify what type of arrhythmia was initially detected based on the PPG signal.

The ECG segments used to generate the ECG based statistical model are preferably obtained using an ECG sensor that is the same or similar to the ECG sensor of the user wearable device (e.g., 102) that will be used to monitor for arrhythmias, or the ECG segments preferably resemble the ECG waveforms that can be obtained using the ECG sensor 128 of the user wearable device (e.g., 102) that will be used to monitor for arrhythmias. Additionally, the PPG segments used to generate the PPG based statistical model are preferably obtained using a PPG sensor that is the same or similar to the PPG sensor (e.g., 122) of the user wearable device (e.g., 102) that will be used to monitor for arrhythmias, or the PPG segments preferably resemble the PPG waveforms that can be obtained using the PPG sensor (e.g., 122) of the user wearable device (e.g., 102) that will be used to monitor for arrhythmias.

In addition to or instead of using PPG and ECG based statistical models to detect an arrhythmia, and to confirm or reject the detection of the arrhythmia, machine learning models can be used to perform these functions. In other words, a PPG based machine learning model and/or an ECG based machine learning model can additionally, or alternatively, be used to detect an arrhythmia, and confirm or reject the detection of the arrhythmia. Accordingly, the block 502 can be referred to as an ECG based statistical and/or machine learning model generator, and the block 504 can be referred to as a PPG based statistical and/or machine learning model generator. Additionally, the block 512 can be referred to as an ECG based statistical and/or machine learning model, and the block 514 can be referred to as a PPG based statistical and/or machine learning model. Such machine learning models can be similarly generated based on PPG and ECG data sets, examples of which were discussed above. In accordance with certain embodiments, an ECG data engine or model generator can be used to generate the ECG based machine learning model based on the ECG data set, and a PPG data engine or model generator can be used to generate the PPG based machine learning model based on the PPG data set. More generally, an ECG based machine learning model can be trained based on an ECG data set (and optionally based on one or more further types of data sets), and a PPG based machine learning model can be trained based on a PPG data set (and optionally based on one or more further types of data sets). These machine learning models can be implemented by the arrhythmia detector 228 of the user-wearable device 102. In certain embodiments, the PPG based machine learning model can be used to generally detect an arrhythmia (e.g., without any specificity as to the type) based on a PPG signal, and then the ECG based machine learning model (after an ECG signal is obtained) can be used to perform arrhythmia discrimination (alone or in combination with the PPG based machine learning model and/or a BP based machine learning model) to classify what type of arrhythmia was initially detected based on the PPG signal.

The PPG based statistical and/or machine learning model 514 can be generated and/or trained using one or more other types of sensor signals (in addition to PPG signals) obtained using one or more other types of sensors, such as, but not limited to, skin temperature, bioimpedance, galvanic skin resistance, or actigraphy. For example, a skin temperature data set, bioimpedance data set, galvanic skin resistance data set, and/or actigraphy data set corresponding to NSR, and corresponding to each of a plurality of arrhythmias of potential interest, such as, but not limited to, AF, AFL, PACs, PVCs, VT, and/or VF, can be provided to the model 514. This enables the model 514 to also use (in addition to a PPG signal) other types of sensor signals/data to detect an arrhythmia, such as AF. Similarly, the ECG based statistical and/or machine learning model 512 can be generated and/or trained using one or more other types of sensor signals (in addition to ECG signals) obtained using one or more other types of sensors, such as, but not limited to, skin temperature, bioimpedance, galvanic skin resistance, and/or actigraphy. This enables the model 512 to also use (in addition to an ECG signal) other types of sensor signals/data to confirm or reject the detection arrhythmia, such as AF, and/or perform arrhythmia discrimination. Examples of sensors that can be used to obtain such additional types of signals were discussed above, e.g., with reference to FIGS. 1A-1C, and 2. As shown in FIG. 5, an ECG data set can be provided to the PPG based statistical and/or machine learning model generator 502, and a PPG data set can be provided to the ECG based statistical and/or machine learning model generator 504, either directly, or via the model supervisor 506, depending upon the specific implementation.

It is believed that a person's blood pressure may be affected differently by different arrhythmias in different manners. For example, some arrhythmias may increase blood pressure, while others may reduce blood pressure, and still others may not change a person's blood pressure. Further, certain arrhythmias may increase or decrease a person's blood pressure by different extents. In accordance with certain embodiments of the present technology, the BP sensor 230 is used to determine a measure of blood pressure of a user (i.e., wearer) of the user-wearable device 102 (based on PPG and ECG signals obtained respectively by the PPG and ECG sensors 122 and 128), and the measure of blood pressure is provided to and used by the arrhythmia detector 228 to assist in confirming or rejecting an initial detection of an arrhythmia based solely on a PPG signal. In other words, after an ECG signal is obtained, following the initial detection of an arrhythmia based on a PPG signal, the ECG signal itself can be analyzed to confirm or reject the detection of the arrhythmia based on the PPG signal, and the ECG and PPG signals can both be used to determine a measure of blood pressure that can also be used to confirm or reject the detection of the arrhythmia based on the PPG signal. A statistical model and/or machine learning model can be provided with a blood pressure measurement to help confirm or reject the detection of the arrhythmia based on the PPG signal, and/or to perform arrhythmia discrimination. Instead of determining a measure of blood pressure and using the measure of blood pressure to detect an arrhythmia and/or confirm or reject an arrhythmia detection (and/or perform arrhythmia discrimination), a surrogate of blood pressure can be determined and used in place of a measure of blood pressure. Exemplary surrogates (aka proxies) of blood pressure were discussed above. One or more additionally and/or alternative surrogates of blood pressure can also be used, which surrogates can be obtained from a PPG signal, an ECG signal, and/or from other sensor signals.

Figure 6:
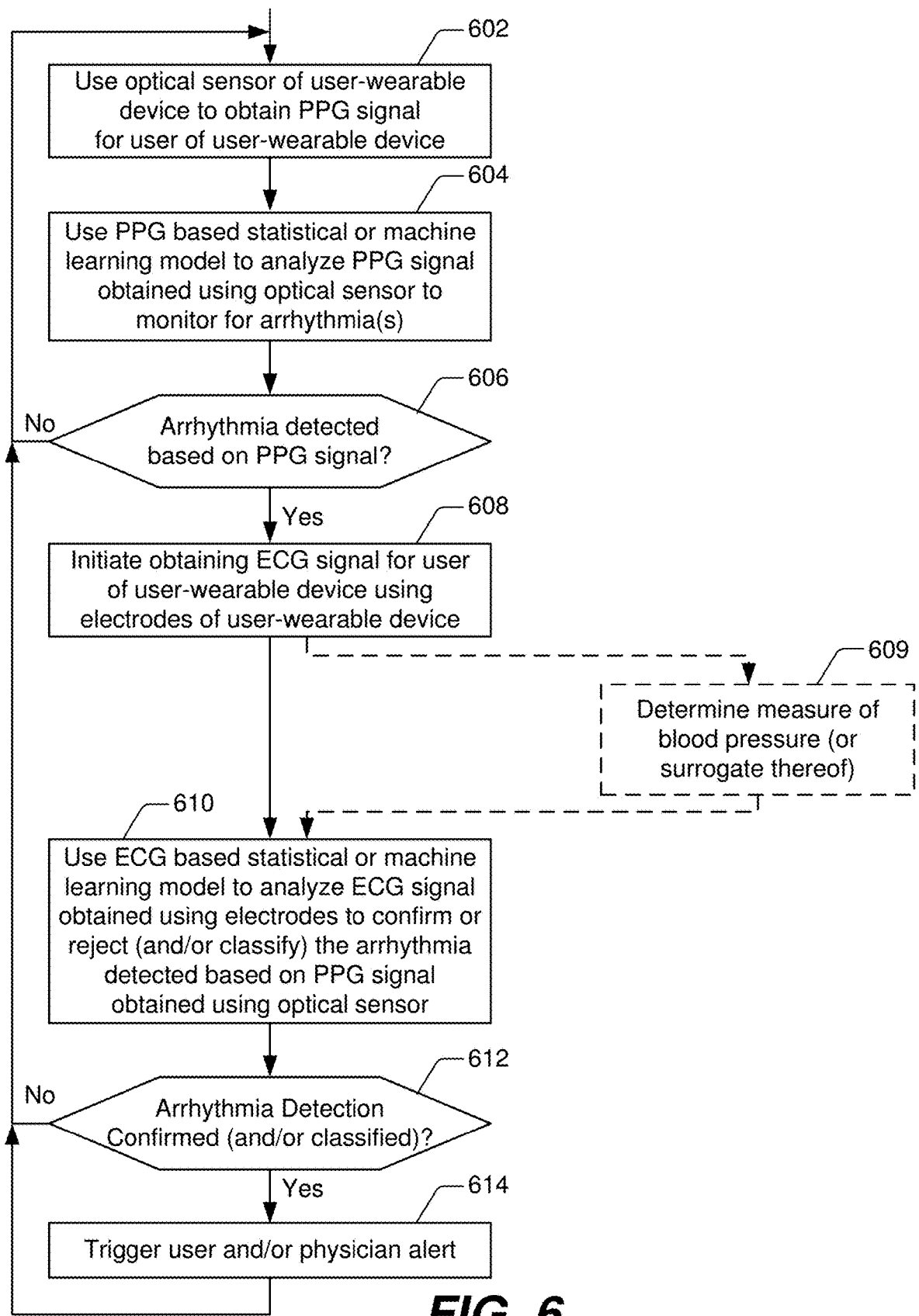
FIG. 6 is a high level flow diagram that is used to summarize methods according to various embodiments of the present technology.

FIG. 6 is a high level flow diagram that is used to summarize certain methods for monitoring for arrhythmias including AF based on a PPG signal obtained using an optical sensor of a user-wearable device. Such methods are for use by a user-wearable device (e.g., 102) including an optical sensor (e.g., 122) to obtain a PPG signal, and electrodes (e.g., 114 and 134) to obtain an electrocardiogram (ECG) signal.

Referring to FIG. 6, step 602 involves using the optical sensor of the user-wearable device to obtain a PPG signal for a user of the user-wearable device. A PPG signal can be obtained continually or substantially continually. However, since it takes power to drive a light source of an PPG sensor (e.g., 122, also referred to more generally as an optical sensor), as well as to analyze a PPG signal, battery life (e.g., between recharging or replacement) can be extended by selectively obtaining a PPG signal at step 602, e.g., periodically, during specific times of the day, during the detection of motion or lack thereof, or in response to some other triggering event (e.g., such as detecting a certain level of stress, or the like). More generally, PPG data acquisition can be automatically or manually initiated to monitor heart rate for a selected period of time.

Step 604 includes using a PPG based statistical or machine learning model to analyze the PPG signal obtained using the optical sensor to monitor for one or more types of arrhythmias including AF. Exemplary details of how such a model can be generated and used were discussed above, e.g., with reference to FIG. 5. A time period during which a PPG signal is obtained and analyzed to monitor for one or more types of arrhythmias can be referred to as a PPG monitoring period. During a PPG monitoring period, the beat-to-beat pattern can be characterized by extracting certain features of the PPG waveform of every beat, on a beat-to-beat basis, as well as specific features of a sequence of beat-to-beat waveforms, or multiple sequences of these beat-to-beat waveforms. In accordance with an embodiment, the single beat waveform, beat-to-beat sequence and/or multi-beat sequence, along with related PPG pattern features, can be used to infer the probability of an arrhythmic event. Upon such an inference, the user (i.e., wearer of the user-wearable device) may be directed to take further action to enable the device to obtain and monitor the user's ECG signal under a specific timeframe guidance by the device, e.g., as described below with reference to steps 606 and 608.

In accordance with certain embodiments, increases in body temperature (e.g., determined using the skin temperature sensor 130) beyond a threshold (or by more than a threshold amount within a specified amount of time) can be used to trigger PPG data acquisition at step 602 and arrhythmia monitoring at step 604, and/or increase the frequency of PPG data acquisition at step 602 and arrhythmia monitoring at step 604, since increases in body temperature can increase the probability of AF and/or other types of arrhythmias, and/or may be indicative of AF and/or other types of arrhythmias occurring.

In accordance with certain embodiments, decreases in body water content (e.g., determined using the BIA sensor 120) beyond a threshold (or by more than a threshold amount within a specified amount of time) can be used to trigger PPG data acquisition at step 602 and arrhythmia monitoring at step 604, and/or increase the frequency of PPG data acquisition at step 602 and arrhythmia monitoring at step 604, since a decrease on body water content associated with dehydration can trigger an arrhythmia.

Still referring to FIG. 6, as can be appreciated from steps 606 and 608, in response to detecting an arrhythmia based on the PPG signal obtained using the optical sensor (e.g., 122), there is an initiating of obtaining of an ECG signal for the user of the user-wearable device using the electrodes of the user-wearable device. Where the user-wearable device is a wrist worn device, step 608 can involve triggering a notification that instructs the user of the user-wearable device to touch one of the electrodes of the user-wearable device with a finger on a hand of an arm opposite an arm on which the user-wearable device is being worn. In other words, the notification can instruct the user of the user-wearable device to touch one of the electrodes of the user-wearable device with a finger on a hand of an arm on which the user-wearable device is not being worn. Such a notification can be a visual, auditory and/or tactile notification. A visual notification can be, e.g., text and/or an image displayed on the display (e.g., 108) of a user-wearable device (e.g., 102), or can be a simple as illuminating a light emitting diode (LED), or the like. An auditory notification can be, e.g., a buzzing or other type of alarm, or can be prerecorded or computer generated verbal instructions. A tactile notification can be, e.g., a vibratory alert. As noted above, if a user is wearing the device 102 on their left arm (so that an electrode on the backside of the housing is in contact with the user's left wrist), then the user must touch the front facing electrode 114 (or some other accessible second electrode) with a finger on their right arm in order for the device to obtain an ECG signal. If a user is wearing the device 102 on their right arm, then the user must touch the front facing electrode 114 (or some other accessible second electrode) with a finger on their left arm in order for the device to obtain an ECG signal.

Simultaneous with and/or soon after obtaining a PPG signal at step 602, one or more further signals may be obtained, such as, but not limited to a skin temperature signal, bioimpedance signal, galvanic skin resistance signal, and/or actigraphy signal, and at step 604 the model can use one or more of such further signals to monitor for arrhythmia(s). In such an embodiment, the decision at step 606 can also be based on such further signal(s). While not specifically shown in the high level flow diagram of FIG. 6, in response to an arrhythmia being detected at step 606, raw and/or processed PPG data can be stored, as can raw and/or processed data corresponding to one or more of skin temperature, bioimpedance, galvanic skin resistance, actigraphy signal, and/or one or more other signals so that such newly stored data can be used to update and improve the model 514.

Step 610 involves using an ECG based statistical or machine learning model to analyze the ECG signal obtained using the electrodes of the user-wearable device to confirm or reject the detecting of the arrhythmia based on the PPG signal obtained using the optical sensor. Additionally or alternatively, the ECG based statistical or machine learning model can be used to perform arrhythmia discrimination (alone or in combination with the PPG based statistical or machine learning model) to classify what type of arrhythmia was initially detected based on the PPG signal.

A time period during which an ECG signal is obtained and analyzed to monitor for one or more types of arrhythmias can be referred to as an ECG monitoring period. Depending upon the specific user-wearable device, ECG signal and data acquisition can be automatically or manually initiated. For example, in certain embodiments, e.g., such as when an ECG signal is to be obtained using the user-wearable device 102 described above, the device wearer needs to follow certain instructions to acquire an ECG signal, which may take place for a selected period of time. In certain embodiments, an ECG signal can be obtained in response to a PPG monitoring event guidance or at any opportune time the user would like to initiate and gather ECG data. During an ECG monitoring period, ECG patterns can also be characterized by extracting certain features from a single beat waveform, beat-to-beat sequence and/or multi-sequence waveforms. In accordance with an embodiment, a single beat waveform, beat-to-beat sequence and/or multi-sequence, along with related ECG pattern features, can be used to infer the probability or confirm the presence or absence of an arrhythmia event depending on the amount of arrhythmic data present at the time of ECG monitoring. Upon such an inference, or confirmation, the user may be directed to take an action relative to pursuing a more extensive medical evaluation and/or to further monitor the user's ECG signal under a specific timeframe guidance by the device, e.g., as described below with reference to step 614.

As shown at step 609, a measure of blood pressure can be determined based on the PPG and ECG signals obtained, respectively, using the optical sensor and the electrodes of the user-wearable device. In accordance with certain embodiments, the measure of blood pressure can also be used (i.e., in addition to using the ECG signal obtained using the electrodes) to confirm or reject the detection of the arrhythmia based on the PPG signal obtained using the optical sensor. Instead of (or in addition to) determining a measure of blood pressure, a surrogate of blood pressure can be determined and used to confirm or reject the detection of the arrhythmia. It would also be possible to use a surrogate of blood pressure to assist with the detection of the arrhythmia at step 606.

In accordance with certain embodiments, simultaneous with or within a short time (i.e., a few seconds) of confirming or rejecting the detection of the arrhythmia, a segment of the ECG signal obtained using the electrodes, or data indicative thereof, is stored in the memory of the user-wearable device. This will enable the ECG signal segment to be available for uploading, viewing and/or analysis by a physician (e.g., a cardiologist) at a later time. In certain embodiments, the ECG signal segment is only stored if the detection of the arrhythmia was confirmed.

Still referring to FIG. 6, in accordance with certain embodiments, if the arrhythmia detection is confirmed, an alert is triggered, as can be appreciated by steps 612 and 614. The alert can be provided to the user wearing the user-wearable device and/or a physician (e.g., a cardiologist). The alert provided to the user can be implemented via a user interface of the user-wearable device (e.g., 102), such as, but not limited to, a display (e.g., 108), a light emitting diode (LED), a speaker, or a vibratory transducer. Accordingly, the alert can be visual, auditory and/or tactile. An alert can be sent to a physician, e.g., using a wireless interface (e.g., 208) of a user-wearable device (e.g. 102), but is not limited thereto. The user alert can, e.g., inform a user that they should contact a physician, go to a hospital, or the like. The user alert may also inform a user to stop operating heavy machinery, such as an automobile or other vehicle. The physician alert can inform a physician of what arrhythmia was detected, as well as identify the person, and potentially the location of the person, if the user wearable device has location identification technology.

Whether or not an arrhythmia is detected and confirmed can be considered binary actions, i.e., an arrhythmia is either detected or not, and a detected arrhythmia is either confirmed or not (i.e., rejected). When a detected arrhythmia is confirmed, an alert can be triggered, as indicated at step 614 in FIG. 6. It would also be possible to determine whether a near-arrhythmia detection occurred, and/or whether a near-arrhythmia confirmation occurred, and store corresponding information, and/or provide alerts based on such "near" detections or confirmations, especially if it is determined that a person is slowly trending towards getting closer to having arrhythmic events and/or having more frequent arrhythmic events. Such information may be useful to a person and/or their physician and may provide a good predictor that arrhythmic events are likely to occur in the near future, and/or increase in their frequency. Accordingly, in certain embodiments the models 512 and/or 514 can be generated to identify such "near" detections and/or "near" confirmations. For an example, a detected heart rate may need to exceed some predetermined threshold rate for a specific type of arrhythmia to be detected and/or confirmed. If a person's heart rate is just below the threshold rate, a "near" detection and/or near "confirmation" of the specific type of arrhythmia can be recorded and/or indicated in an alert. How close a parameter needs to be to a threshold for a "near" detection or confirmation to occur can depend on the specific parameter, and can be predetermined, or determined by a model. For another example, a detected heart rate rhythm pattern may also be monitored for a specific type of arrhythmia to be detected and/or confirmed. If the type of pattern and/or duration is just below a particular threshold specification, a "near" detection and/or near "confirmation" of the specific type of arrhythmia can also be recorded and/or indicated in an alert.

In accordance with certain embodiments, the PPG based statistical or machine learning model is updated based on a segment of the PPG signal that caused the detecting of the arrhythmia (and optionally, also based on a segment of the ECG signal that caused the arrhythmia detection to be confirmed or rejected). Additionally, or alternatively, the ECG based statistical or machine learning model can be updated based on a segment of the ECG signal used to detect or reject an arrhythmia detection and/or perform arrhythmia discrimination (and optionally, also based on the segment of the PPG signal that caused the arrhythmia detection). Accordingly, such models can be updated over time such that they become more accurate over time. These models can be implemented using one or more processor (e.g., 204) of a user-wearable device (e.g., 102). A benefit of updating a PPG based statistical or machine learning model based on both PPG and ECG segments is that this enables the model to discover correlations between the two types of signals, e.g., to understand how changes to an ECG waveform (such as ST elevation) may affect and/or be detectable from a PPG waveform. A benefit of updating an ECG based statistical or machine learning model based on both ECG and PPG segments is that this enables the model to discover correlations between the two types of signals, e.g., to understand how changes to a PPG waveform (such as a reduction in area under the curve, or amplitude) may affect and/or be detectable from an ECG waveform.

Simultaneous with and/or shortly after obtaining an ECG signal at step 610, one or more further signals may be obtained, such as, but not limited to a skin temperature signal, bioimpedance signal, galvanic skin resistance signal, and/or actigraphy signal, and at step 610 the model can use one or more of such further signals to confirm or reject a detected arrhythmia, and/or to classify the detected arrhythmia. In such an embodiment, the decision at step 612 can also be based on such further signal(s). While not specifically shown in the high level flow diagram of FIG. 6, in response to an arrhythmia being confirmed at step 612, raw and/or processed ECG data can be stored, as can raw and/or processed data corresponding to one or more of skin temperature, bioimpedance, galvanic skin resistance, actigraphy signal, and/or one or more of other signals so that such newly stored data can be used to update and improve the model 512.

In accordance with certain embodiments, prior to performing the steps described above with reference to FIG. 6, a plurality of ECG signal segments that correspond to each of a normal sinus rhythm (NSR) and to each of the one or more types of arrhythmias (including AF) are obtained, and a plurality of PPG signal segments that correspond to each of the NSR and to each of the one or more types of arrhythmias including AF are obtained, and these ECG and PPG signal segments are used to generate the ECG and PPG based statistical and/or machine learning models respectively based on the obtained ECG and PPG signal segments. As explained above, additional types of signal segments and/or processed data can also be used to generate the ECG and PPG based models. Additional details of how these models can be generated were discussed above, e.g., with reference to FIG. 5. Preferably, but not necessarily, the PPG signal segments (used to train the PPG based model) are obtained at the same time as the ECG signal segments (used to train the ECG based model) that correspond to each of the NSR and to each of the one or more types of arrhythmias including AF.

Instead of using models to detect an arrhythmia based on a PPG signal and/or use an ECG signal confirm or reject an arrhythmia detection (and/or perform arrhythmia discrimination), it would be possible to use other types of data or signal analysis that does not necessarily rely on statistical models and/or machine learning models. For example, in accordance with certain embodiments, ECG arrhythmia data and PPG arrhythmia data can be stored in memory of a user-wearable device, wherein the ECG arrhythmia data is indicative of ECG features that correlate to each of one or more types of arrhythmias including AF, and the PPG arrhythmia data is indicative of PPG features that correlate to each of the one or more types of arrhythmias including AF. An optical sensor of the user-wearable device can be used to obtain a PPG signal for a user of the user-wearable device, and arrhythmia monitoring can be performed based on the PPG signal obtained using the optical sensor by comparing in real-time or near real-time features of the PPG signal, obtained using the optical sensor of the user-wearable device, to the PPG features indicated in the stored PPG data that correlate to each of the one or more types of arrhythmias including AF. Then, in response to detecting an arrhythmia based on the PPG signal obtained using the optical sensor, obtaining of an ECG signal can be initiated for the user of the user-wearable device using the electrodes of the user-wearable device. Example of how this can be done were discussed above. Features of the ECG signal, obtained using the electrodes of the user-wearable device, can be compared to the ECG features indicated in the stored ECG data, to thereby confirm or reject the detecting of the arrhythmia based on the PPG signal obtained using the optical sensor (and/or to perform arrhythmia discrimination). Further, the ECG arrhythmia data and/or the PPG arrhythmia data stored in the memory of the user-wearable device can be updated based on a segment of the PPG signal that caused the detecting of the arrhythmia and/or based on a segment of the ECG signal that was used to confirm or reject the detecting of the arrhythmia (and/or to perform arrhythmia discrimination). This would enable the device to improve its detections over time. As with the other embodiments described above, a measure and/or surrogate of blood pressure can also be determined based on an ECG and PPG signal, and the measure and/or surrogate of blood pressure can be used to help confirm or reject an arrhythmia detection (and/or to perform arrhythmia discrimination). As with the other embodiments described above, additional types of signals, such as a skin temperature signal, bioimpedance signal, galvanic skin resistance signal, and/or actigraphy signal, can also be used to detect an arrhythmia, confirm or reject a detected arrhythmia, and/or classify a detected arrhythmia. As with the other embodiments described above, user and/or physician alerts can be triggered in response to an arrhythmia detection being confirmed. Examples of PPG and ECG features that can be stored and used to detect and confirm or reject arrhythmia detections (and/or to perform arrhythmia discrimination) were described above, and thus, need not be described again.

In the above described embodiments, PPG and ECG signals were described as being obtained using a same user-wearable device. In alternative embodiments, a PPG signal can be obtained using a first user-wearable device, and an ECG signal can be obtained using a second user-wearable device that can communicate with the first user-wearable device. Other variations are also possible.

In the above described embodiments, following detecting of an arrhythmia based on a PPG signal, an ECG signal was described as being obtained using one or more electrodes (e.g., 134) on a caseback of a wrist-worn device (e.g., 102), and a front facing electrode (e.g., 114) that needs to be touched by a finger on an opposite hand of the arm on which the device is being worn. This is used to complete a circuit between which the user's heart is located. In alternative embodiments, where the ECG signal can be obtained from a device being worn on a user's chest, such a device can be used to obtain an ECG signal on demand using at least a pair of electrodes of the device, without requiring that the user do anything, such as touch something with their hand.

In accordance with certain embodiments of the present technology, in order to characterize a combined PPG-ECG pattern, PPG and ECG signals can be recorded simultaneously or separately. In either case, there is a set of features that can relate to a combined pattern behavior for both types of signals. A stronger arrhythmia correlation will potentially occur when both signals are monitored concurrently. The combined single beat and beat-to-beat sequence or sequences, and the cross modality combined pattern features that can be obtained through various tools and techniques including statistical tools, machine learning techniques and other methods, represent a unique advantage of such embodiments of the present technology, as the individual PPG and ECG pattern features along with the combined PPG and ECG pattern features can provide a strong unique marker for an individual. This pattern is not expected to change much in the short term, when monitoring during a similar physiological state. The pattern may, however, change with time under acute physiological changes of the individual, and return to normalcy after the acute event elapses. In the long run, this pattern is expected to evolve along with the physiology of the individual. A device that implements the present technology, such as the device 102 described above, and the related data and analytical engines enable the creation and adaptation of this pattern for a given individual through time. This gives this pattern a dynamic character that can be used for various purposes and can encapsulate the ECG/PPG marker for an individual at a particular time frame and as a function of time.

As noted above, a PPG signal (e.g., sensed using the optical sensor 122) can be used as a biometric signal that is used to determine whether or not to authenticate a user. Additionally, or alternatively, an ECG signal can be used for user authentication. The uniqueness of PPG, ECG and combined ECG/PPG signal patterns for an individual may be used to authenticate the individual for various different purposes. One scenario, is to manage the flow of information from a particular data collection episode as to whether the flow up to a third party, such as a medical professional, as well as to a secure database repository where the data may either be accessed for medical evaluation of the individual, or other databases that may be accessed for the purpose of data mining and/or physiological model updates or for machine learning engines. Individual PPG, ECG and combined ECG-PPG models can incorporate the user authentication/data validation that can be derived through these models to inform the decision making process as to how to make use and manage these data sets. In accordance with certain embodiments, authentication can also be used to determine if a data set obtained by a user wearable device (and used to improve or otherwise update one or more models) is from the normal user of the device, or from another user who may be borrowing the device from the normal user. Such a data set can be treated differently by one or more models depending on whether the data set corresponds to the normal user of the device or some other user.

In many of the embodiments described above, a PPG signal was described as being initially used to detect an arrhythmia, and an ECG signal was described as being used to confirm or reject the arrhythmia detection and/or to perform arrhythmia discrimination. It is also within the scope of certain embodiments described herein that an arrhythmia can be initially detected based on an ECG signal (e.g., that the user decided on their own to obtain because they felt dizzy or ill, or for any other reason), and that ECG and/or PPG based models can be updated based on such an ECG signal or segment thereof. Further, after an arrhythmia is initially detected based on an ECG signal, a PPG signal (obtained simultaneously with, just prior to, or just after the arrhythmia detection) can be used to reject or confirm the arrhythmia detection and/or to perform arrhythmia discrimination, as well as to update the PPG and/or ECG based models.

In accordance with certain embodiments of the present technology, a single beat PPG waveform, beat-to-beat sequence or multi-sequence, along with related PPG pattern features can be used to ascertain a subset of these features to establish a unique set of PPG waveform characteristics that can be associated with a user. This unique set of personal features can then be associated with the individual as well as with the timeframe in which the data collection takes place. The timeframe can serve as a clear indicator in the short term, as to indicate the time of the day relative to a particular event that may have an impact on the individual's physiological state, including the circadian cycle, as well as in the long term, as the unique PPG pattern may change with time.

Additionally, or alternatively, a single beat ECG waveform, beat-to-beat sequence or multi-sequence, along with related ECG pattern features can also be used to ascertain a subset of these features to establish a unique set of ECG waveform characteristics that can be associated with the user. This unique set of personal features can then be associated with the individual as well as with the timeframe in which the data collection takes place. The timeframe can serve as a clear indicator in the short term, as to indicate the time of the day relative to a particular event that may have an impact on the individual's physiological state, including the circadian cycle, as well as in the long term, as the unique ECG pattern may change with time.

A cardiac arrhythmia can result from various factors, including, but not limited to, predisposing comorbidities, lifestyle and surgery. Among the comorbidities that increase the risk of AF, are cardiovascular conditions, including hypertension, coronary artery disease and structural heart disease. Current studies of AF also include the role of the autonomic nervous system. Certain embodiments of the present technology provide for the ability to monitor HRV by using the beat-to-beat heart rate signal through the PPG modality. Such embodiments also provide the ability to monitor HRV based on an ECG signal after a PPG monitoring event infers the probability of an arrhythmic event or at other times, through normal baseline data collection routines. Certain embodiments further provide the ability to monitor blood pressure, based on PTT or PWV. Certain embodiments also provide the ability to monitor sleep and sleep quality (efficiency) and physical activity levels, which have a key impact in overall health. The ECG and PPG signals can be used by a physiological engine, along with sleep metrics and physical activity levels, that works in conjunction with the arrhythmia statistic/machine learning analytical modules, to assist in the inference and or confirmation of an arrhythmic event.

It is noted that the term based on, as used herein, means based at least in part on, unless stated otherwise. In other words, if a decision is based on certain data, that means the decision is based at least in part on the certain data and can also be based on additional data.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen to best explain the principles of the technology and its practical application to thereby enable others skilled in the art to best utilize the technology in various embodiments and with various modifications as are suited to the particular use contemplated. It is intended that the scope of the technology be defined by the claims appended hereto. While various embodiments have been described above, it should be understood that they have been presented by way of example, and not limitation. It will be apparent to persons skilled in the relevant art that various changes in form and detail can be made therein without departing from the spirit and scope of the technology. The breadth and scope of the present technology should not be limited by any of the above-described exemplary embodiments, but should be defined only in accordance with the following claims and their equivalents.

What is claimed is:

1. A method for monitoring for one or more types of arrhythmias including atrial fibrillation (AF) based on a photoplethysmography (PPG) signal obtained using an optical sensor of a user-wearable device, the method comprising:
   using the optical sensor to obtain a PPG signal for a user;
   using at least one of a PPG based statistical or machine learning model to analyze the PPG signal obtained using the optical sensor to monitor for one or more types of arrhythmias including atrial fibrillation (AF);
   in response to the at least one of the PPG based statistical or machine learning model being used to detect an arrhythmia based on the PPG signal obtained using the optical sensor, initiating obtaining of an electrocardiogram (ECG) signal using electrodes of an ECG sensor; and
   after the at least one of the PPG based statistical or machine learning model has been used to detect the arrhythmia based on the PPG signal obtained using the optical sensor, using at least one of an ECG based statistical or machine learning model to analyze the ECG signal obtained using the electrodes of the ECG sensor to confirm or reject the detecting of the arrhythmia.

2. The method of claim 1, further comprising:
   using one or more further sensors to obtain one or more further sensor signals indicative of one or more of skin temperature, bioimpedance, galvanic skin resistance, or actigraphy; and
   wherein the using the at least one of the PPG based statistical or machine learning model to analyze the PPG signal also includes using the at least one of the PPG based statistical or machine learning model to analyze at least one of the one or more further sensor signals indicative of one or more of skin temperature, bioimpedance, galvanic skin resistance, or actigraphy to monitor for the one or more types of arrythmias including AF.

3. The method of claim 1, further comprising:
   using one or more further sensors to obtain one or more further sensor signals indicative of one or more of skin temperature, bioimpedance, galvanic skin resistance, or actigraphy; and
   wherein the using the at least one of the ECG based statistical or machine learning model to analyze the ECG signal also includes using the at least one of the ECG based statistical or machine learning model to analyze at least one of the one or more further sensor signals indicative of one or more of skin temperature, bioimpedance, galvanic skin resistance, or actigraphy to confirm or reject the detecting of the arrhythmia based on the PPG signal obtained using the optical sensor.

4. The method of claim 1, wherein the ECG sensor is also part of the same user-wearable device that includes the optical sensor, wherein one of the electrodes used to obtain an ECG signal is in contact with a user's arm or wrist whenever the user is wearing the user-wearable device, and wherein the initiating obtaining of an ECG signal for the user of the user-wearable device, in response to detecting an arrhythmia based on the PPG signal obtained using the optical sensor, comprises:
   triggering a notification that instructs the user of the user-wearable device to touch another one of the electrodes of the user-wearable device with a finger on a hand of an arm opposite an arm on which the user-wearable device is being worn;
   wherein the notification is one of a visual, auditory or tactile notification.

5. The method of claim 1, further comprising simultaneous with or after confirming or rejecting the detecting of the arrhythmia storing the following in memory of the user wearable device:
   a segment of the ECG signal obtained using the electrodes and/or data indicative thereof; and
   a segment of the PPG signal obtained using the optical sensor and/or data indicative thereof.

6. The method of claim 1, further comprising at least one of the following:

updating the at least one of the PPG based statistical or machine learning model based on a segment of the PPG signal that caused the detecting of the arrhythmia;

updating the at least one of the ECG based statistical or machine learning model based on a segment of the ECG signal that caused the detection of the arrhythmia, based on the PPG signal, to be confirmed or rejected;

updating the at least one of the PPG based statistical or machine learning model based on the segment of the PPG signal that caused the detecting of the arrhythmia as well as based on a segment of an ECG signal that caused the arrhythmia detection to be confirmed or rejected; or updating the at least one of the ECG based statistical or machine learning model based on the segment of the ECG signal that caused the arrhythmia detection to be confirmed or rejected as well as based on the segment of the PPG signal that caused the detection of the arrhythmia.

7. The method of claim 6, further comprising:

using at least one of the obtained PPG signal, the obtained ECG signal, or other signals obtained using other sensors of the user-wearable device to perform an authentication process to determine whether or not a wearer of the user-wearable device is a normal wearer of the user-wearable, and based on results thereof, performing the updating such that the updating is performed in a first manner when the wearer is the normal wearer, and the updating is performed in a second manner when the wearer is not the normal wearer.

8. The method of claim 1, wherein the user-wearable device includes one or more processors that is/are used to implement the at least one of the PPG based statistical or machine learning model and the at least one of the ECG based statistical or machine learning model.

9. The method of claim 1, further comprising, prior to using at least one of a PPG based statistical or machine learning model to monitor for one or more types of arrhythmias:

obtaining a plurality of ECG signal segments that correspond to each of a normal sinus rhythm (NSR) and to each of the one or more types of arrhythmias including AF;

obtaining a plurality of PPG signal segments that correspond to each of the NSR and to each of the one or more types of arrhythmias including AF;

generating the at least one of the PPG based statistical or machine learning model based on the obtained PPG signal segments; and generating the at least one of the ECG based statistical or machine learning model based on the obtained ECG signal segments.

10. The method of claim 1, further comprising:

determining a measure of blood pressure or a surrogate of blood pressure based on at least one of the PPG or ECG signals obtained, respectively, using the optical sensor and the electrodes of the user-wearable device; and also using the measure of blood pressure or the surrogate of blood pressure to confirm or reject the arrhythmia detection based on the PPG signal obtained using the optical sensor.

11. The method of claim 1, wherein the ECG sensor is not part of the same user-wearable device that includes the optical sensor.

12. The method of claim 1, further comprising:

triggering a first alert, to at least one of a wearer of the user-wearable device or a medical personnel, in response to an arrhythmia being detected and confirmed;

identifying one or more near detections of an arrhythmia and/or near confirmations of one or more detected arrhythmias; and triggering a second alert, to at least one of the wearer of the user-wearable device or the medical personnel, based on the one or more near detections of an arrhythmia and/or the near confirmations of one or more detected arrhythmias.

13. The method of claim 1, further comprising initiating obtaining of a further ECG signal and a corresponding further PPG signal, in response to either a user request, a third party request, or a trigger; and further comprising at least one of the following:

updating the at least one of the PPG based statistical or machine learning model based on the further PPG signal; or updating the at least one of the ECG based statistical or machine learning model based on the further ECG signal.

14. A user-wearable device, comprising:

an optical sensor including a light source and a light detector and configured to obtain a photoplethysmography (PPG) signal;

an electrocardiogram (ECG) sensor including electrodes and configured to obtain an electrocardiogram (ECG) signal; and an arrhythmia detector configured to use at least one of a PPG based statistical or machine learning model to monitor for one or more types of arrhythmias including atrial fibrillation (AF) based on a PPG signal obtained using the optical sensor;

initiate obtaining of an ECG signal for the user of the user-wearable device using the electrodes of the ECG sensor of the user-wearable device, in response to an arrhythmia being detected using the at least one of the PPG based statistical or machine learning model based on the PPG signal obtained using the optical sensor; and use at least one of an ECG based statistical or machine learning model to analyze an ECG signal obtained using the electrodes to confirm or reject a detection of an arrhythmia based on a PPG signal obtained using the optical sensor, after the at least one of the PPG based statistical or machine learning model has been used to detect the arrhythmia.

15. The user-wearable device of claim 14, further comprising:

one or more further sensors configured to obtain one or more further sensor signals indicative of one or more of skin temperature, bioimpedance, galvanic skin resistance, or actigraphy;

wherein the at least one of the PPG based statistical or machine learning model is also configured to analyze at least one of the one or more further sensor signals indicative of one or more of skin temperature, bioimpedance, galvanic skin resistance, or actigraphy to monitor for the one or more types of arrythmias including AF.

16. The user-wearable device of claim 14, further comprising:
one or more further sensors configured to obtain one or more further sensor signals indicative of one or more of skin temperature, bioimpedance, galvanic skin resistance, or actigraphy;
wherein the at least one of the ECG based statistical or machine learning model is also configured to analyze at least one of the one or more further sensor signals indicative of one or more of skin temperature, bioimpedance, galvanic skin resistance, or actigraphy to confirm or reject the detecting of the arrhythmia based on the PPG signal obtained using the optical sensor.

17. The user-wearable device of claim 14, wherein:
one of the electrodes of the ECG sensor is configured to be in contact with a user's arm or wrist whenever the user is wearing the user-wearable device; and
the arrhythmia detector is configured to initiate obtaining of an ECG signal for the user of the user-wearable device using the ECG sensor of the user-wearable device, in response to an arrhythmia being detected based on the PPG signal obtained using the optical sensor, by triggering a visual, auditory or tactile notification that instructs the user of the user-wearable device to touch another one of the electrodes of the user-wearable device with a finger on a hand of an arm opposite an arm on which the user-wearable device is being worn.

18. The user-wearable device of claim 14, further comprising memory that stores the following:
a segment of the ECG signal obtained using the electrodes and/or data indicative thereof; and
a segment of the PPG signal obtained using the optical sensor and/or data indicative thereof.

19. The user-wearable device of claim 14, wherein the arrhythmia detector is also configured to at least one of:
update the at least one of the PPG based statistical or machine learning model based on a segment of the PPG signal that caused the detecting of the arrhythmia;
update the at least one of the ECG based statistical or machine learning model based on a segment of the ECG signal that caused the detection of the arrhythmia, based on the PPG signal, to be confirmed or rejected;
update the at least one of the PPG based statistical or machine learning model based on the segment of the PPG signal that caused the detecting of the arrhythmia as well as based on a segment of an ECG signal that caused the arrhythmia detection to be confirmed or rejected; or
update the at least one of the ECG based statistical or machine learning model based on the segment of the ECG signal that caused the arrhythmia detection to be confirmed or rejected as well as based on the segment of the PPG signal that caused the detection of the arrhythmia.

20. The user-wearable device of claim 14, wherein the arrhythmia detector, including its use of the at least one of the PPG based statistical or machine learning model and the at least one of the ECG based statistical or machine learning model, is implemented using one or more processors of the user-wearable device.

21. The user-wearable device of claim 14, further comprising:
a blood pressure (BP) detector configured to determine a measure of blood pressure or a surrogate of blood pressure based on at least one of the PPG and ECG signals obtained, respectively, using the optical and ECG sensors of the user-wearable device; and
wherein the arrhythmia detector is also configured to use the measure of blood pressure or the surrogate of blood pressure to help confirm or reject the arrhythmia detection based on the PPG signal obtained using the optical sensor.

22. For use by a user-wearable device including memory, an optical sensor configured to obtain a photoplethysmography (PPG) signal, and an electrocardiogram (ECG) sensor configured to obtain an electrocardiogram (ECG) signal, a method for monitoring for one or more types of arrhythmias including atrial fibrillation (AF) based on a PPG signal obtained using the optical sensor of the user-wearable device, the method comprising:
storing ECG arrhythmia data and PPG arrhythmia data in the memory of the user-wearable device, the ECG arrhythmia data indicative of ECG features and/or ECG signal segments that correlate to each of one or more types of arrhythmias including AF, and the PPG arrhythmia data indicative of PPG features and/or PPG signal segments that correlate to each of the one or more types of arrhythmias including AF;
using the optical sensor of the user-wearable device to obtain a PPG signal for a user of the user-wearable device;
performing arrhythmia monitoring based on the PPG signal obtained using the optical sensor by comparing in real-time or near real-time features and/or signal segments of the PPG signal, obtained using the optical sensor of the user-wearable device, to the PPG features and/or signal segments indicated in the stored PPG data that correlate to each of the one or more types of arrhythmias including AF;
in response to detecting an arrhythmia based on results of the comparing the features and/or signal segments of the PPG signal obtained using the optical sensor to the PPG features and/or signal segments indicated in the stored PPG data that correlate to each of the one or more types of arrhythmias including AF, initiating obtaining of an ECG signal for the user of the user-wearable device using the ECG sensor of the user-wearable device; and
after the arrhythmia has been detected based on the results of the comparing the features and/or signal segments of the PPG signal obtained using the optical sensor to the PPG features and/or signal segments indicated in the stored PPG data that correlate to each of the one or more types of arrhythmias including AF, comparing features and/or signal segments of the ECG signal, obtained using the ECG sensor of the user-wearable device, to the ECG features and/or signal segments indicated in the stored ECG data, to thereby confirm or reject the detecting of the arrhythmia.

23. The method of claim 22, wherein a first electrode of the ECG sensor is configured to be in contact with a user's arm or wrist whenever the user is wearing the user-wearable device; and wherein the initiating obtaining of an ECG signal for the user of the user-wearable device, in response to detecting an arrhythmia based on the PPG signal obtained using the optical sensor, comprises:
triggering a notification that instructs the user of the user-wearable device to touch a second electrode of the ECG sensor of the user-wearable device with a finger on a hand of an arm opposite an arm on which the user-wearable device is being worn;

wherein the notification is one of a visual, auditory or tactile notification.

24. The method of claim 22, further comprising simultaneous with or after confirming or rejecting the detecting of the arrhythmia storing the following in memory of the user wearable device:
- a segment of the ECG signal obtained using the electrodes and/or data indicative thereof; and
- a segment of the PPG signal obtained using the optical sensor and/or data indicative thereof.

25. The method of claim 22, further comprising:
updating the ECG arrhythmia data and the PPG arrhythmia data stored in the memory of the user-wearable device based on a segment of the PPG signal that caused the detecting of the arrhythmia and based on a segment of the ECG signal that was used to confirm or reject the detecting of the arrhythmia.

26. The method of claim 25, wherein:
the user-wearable device includes a processor that uses at least one of statistical modeling or machine learning to identify the PPG features and/or signal segments that correlate to each of the one or more types of arrhythmias including AF, which are the PPG features and/or signal segments indicated in the PPG data stored in the memory of the user-wearable device; and
further comprising updating the at least one of the statistical modeling or machine learning based on a segment of the PPG signal that caused the detecting of the arrhythmia and based on a segment of the ECG signal that was used to confirm or reject the detecting of the arrhythmia.

27. The method of claim 22, further comprising, prior to the performing arrhythmia monitoring:
- obtaining ECG signal segments that correspond to the one or more types of arrhythmias including AF;
- obtaining PPG signal segments that were obtained at the same time as the ECG signal segments that correspond to the one or more types of arrhythmias including AF; and
- using at least one of statistical modeling or machine learning to identify the PPG features and/or signal segments that correlate to each of the one or more types of arrhythmias including AF, which are the PPG features and/or signal segments indicated in the PPG data stored in the memory of the user-wearable device.

28. The method of claim 22, further comprising:
determining a measure of blood pressure or a surrogate of blood pressure based on the PPG and/or ECG signals obtained, respectively, using the optical sensor and the electrodes of the user-wearable device; and
also using the measure of blood pressure or the surrogate of blood pressure to confirm or reject the detecting of the arrhythmia based on the PPG signal obtained using the optical sensor.

29. For use by a user-wearable device including an optical sensor configured to obtain a photoplethysmography (PPG) signal, and an electrocardiogram (ECG) sensor including electrodes and configured to obtain an electrocardiogram (ECG) signal, a method for monitoring for one or more types of arrhythmias including atrial fibrillation (AF) based on a PPG signal obtained using the optical sensor of the user-wearable device, the method comprising:
- using the optical sensor of the user-wearable device to obtain a PPG signal for a user of the user-wearable device;
- using at least one of a PPG based statistical or machine learning model to analyze the PPG signal obtained using the optical sensor to monitor for one or more types of arrhythmias including atrial fibrillation (AF);
- in response to the at least one of the PPG based statistical or machine learning model being used to detect an arrhythmia based on the PPG signal obtained using the optical sensor, initiating obtaining of an ECG signal for the user of the user-wearable device using the electrodes of the ECG sensor of the user-wearable device; and
- after the at least one of the PPG based statistical or machine learning model has been used to detect the arrhythmia based on the PPG signal obtained using the optical sensor, using at least one of an ECG based statistical or machine learning model to analyze the ECG signal obtained using the electrodes of the user-wearable device to perform arrhythmia discrimination and thereby classify the arrhythmia initially detected using the at least one of the PPG based statistical or machine learning model.

30. The method of claim 29, wherein the at least one of the PPG based statistical or machine learning model is also used to classify the arrhythmia.

31. The method of claim 30, further comprising:
determining a measure of blood pressure or a surrogate of blood pressure based on the PPG and ECG signals obtained, respectively, using the optical and ECG sensors of the user-wearable device; and
also using the measure of blood pressure or surrogate of blood pressure to classify the arrhythmia.

\* \* \* \* \*